US012138040B2

(12) United States Patent
Hiyama et al.

(10) Patent No.: US 12,138,040 B2
(45) Date of Patent: Nov. 12, 2024

(54) LOWER LIMB MUSCLE STRENGTH EVALUATION METHOD, NON-TRANSITORY COMPUTER-READABLE RECORDING MEDIUM STORING LOWER LIMB MUSCLE STRENGTH EVALUATION PROGRAM, LOWER LIMB MUSCLE STRENGTH EVALUATION DEVICE, AND LOWER LIMB MUSCLE STRENGTH EVALUATION SYSTEM

(71) Applicant: Panasonic Intellectual Property Corporation of America, Torrance, CA (US)

(72) Inventors: Takahiro Hiyama, Tokyo (JP); Yoshikuni Sato, Tokyo (JP); Jun Ozawa, Nara (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 834 days.

(21) Appl. No.: 16/885,571

(22) Filed: May 28, 2020

(65) Prior Publication Data

US 2020/0375503 A1    Dec. 3, 2020

Related U.S. Application Data

(60) Provisional application No. 62/854,053, filed on May 29, 2019.

(30) Foreign Application Priority Data

Sep. 17, 2019    (JP) .................... 2019-168397

(51) Int. Cl.
*A61B 5/11*    (2006.01)
*G16H 50/20*    (2018.01)
*G16H 50/30*    (2018.01)

(52) U.S. Cl.
CPC ........... *A61B 5/1107* (2013.01); *A61B 5/1113* (2013.01); *A61B 5/1116* (2013.01);
(Continued)

(58) Field of Classification Search
CPC ....... A61B 5/1107; A61B 5/1113–1128; A61B 2562/0219; A61B 5/224; G16H 50/20; G16H 50/30
See application file for complete search history.

(56) References Cited

U.S. PATENT DOCUMENTS 8,574,176 B2 * 11/2013 Sankai ................. A61B 5/1121
601/5
9,403,000 B2 * 8/2016 Lyons ................ A61N 1/37229
(Continued)

FOREIGN PATENT DOCUMENTS

CN    106667727    5/2017
JP    2009-125506    6/2009
(Continued)

OTHER PUBLICATIONS

Seel, et al. "IMU-based joint angle measurement for gait analysis." Sensors 14.4 (2014): 6891-6909. (Year: 2014).*
(Continued)

*Primary Examiner* — David J. McCrosky
(74) *Attorney, Agent, or Firm* — Wenderoth, Lind & Ponack, L.L.P.

(57) ABSTRACT

A lower limb muscle strength evaluation device acquires an angle of at least one of left and right lower limbs of a user while the user stands up from a sitting state, detects at least one lower limb parameter from among a first lower limb maximum value indicating the angle when the lower limb is initially inclined the most in a first direction, a lower limb minimum value indicating the angle when the lower limb is inclined the most in a second direction, a second lower limb
(Continued)

maximum value indicating the angle when the lower limb is again inclined the most in the first direction, a first lower limb elapsed time, a second lower limb elapsed time, and a third lower limb elapsed time, evaluates a lower limb muscle strength of the user using the at least one lower limb parameter, and outputs an evaluation result.

12 Claims, 10 Drawing Sheets

(52) U.S. Cl.
CPC ........... *A61B 5/1127* (2013.01); *G16H 50/20* (2018.01); *G16H 50/30* (2018.01); *A61B 2562/0219* (2013.01)

(56) References Cited

U.S. PATENT DOCUMENTS

| | | | |
|---|---|---|---|
| 10,912,692 B2 * | 2/2021 | Kim | .......................... A61H 3/00 |
| 2011/0082394 A1 | 4/2011 | Chiu et al. | |
| 2012/0289868 A1 | 11/2012 | Chiu et al. | |
| 2017/0128291 A1 | 5/2017 | Kim | |
| 2018/0064599 A1 * | 3/2018 | Kato | .................... A61H 1/0237 |
| 2021/0100704 A1 | 4/2021 | Kim | |

FOREIGN PATENT DOCUMENTS

| | | |
|---|---|---|
| JP | 2011-78731 | 4/2011 |
| KR | 1020160096285 A * | 8/2016 |

OTHER PUBLICATIONS

Morrow, et al. "Validation of inertial measurement units for upper body kinematics." Journal of applied biomechanics 33.3 (2017): 227-232. (Year: 2017).*

Seel, T. et al. "Joint axis and position estimation from inertial measurement data by exploiting kinematic constraints." 2012 IEEE International Conference on Control Applications. IEEE. (Year: 2012).*

Machine translation of KR 20160096285. (Year: 2023).*

* cited by examiner

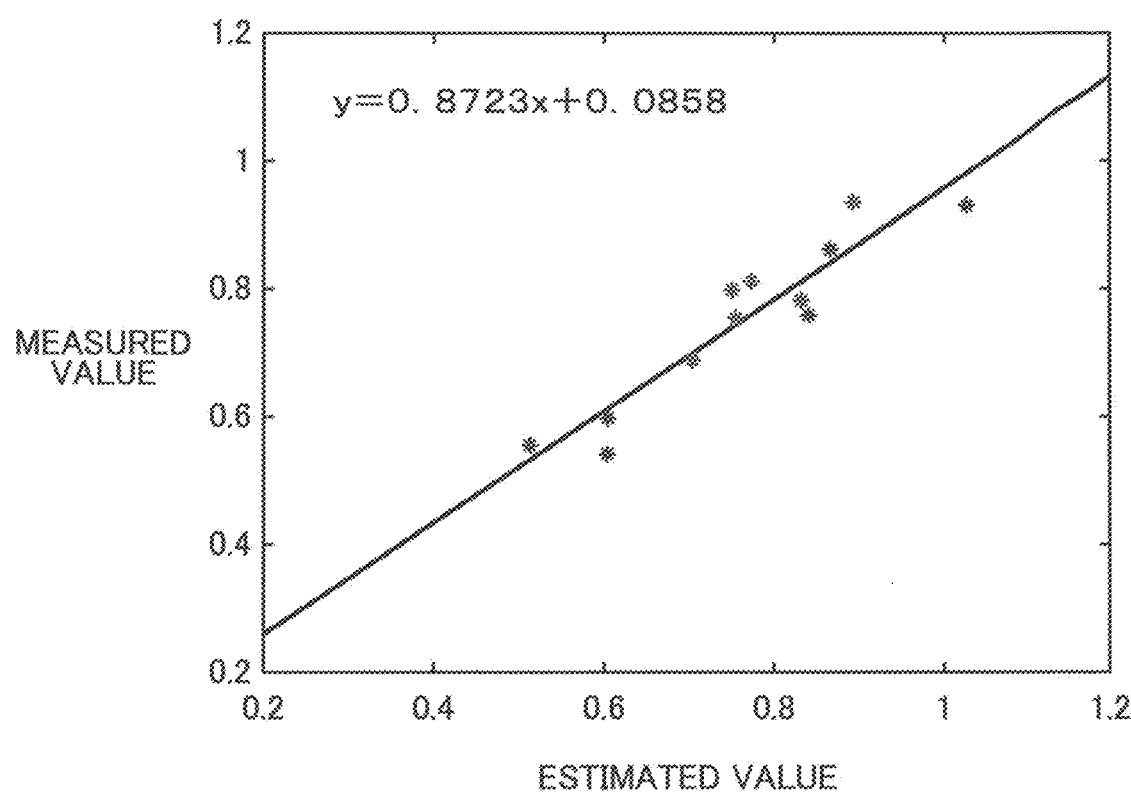

LOWER LIMB MUSCLE STRENGTH EVALUATION METHOD, NON-TRANSITORY COMPUTER-READABLE RECORDING MEDIUM STORING LOWER LIMB MUSCLE STRENGTH EVALUATION PROGRAM, LOWER LIMB MUSCLE STRENGTH EVALUATION DEVICE, AND LOWER LIMB MUSCLE STRENGTH EVALUATION SYSTEM

FIELD OF THE INVENTION

The present disclosure relates to a technology that evaluates the lower limb muscle strength of a user.

BACKGROUND ART

Because falls occur more frequently as people get older, preventing and counteracting falls is an important issue for preventing broken bones or a bedridden state due to falling. The factor that increases falling risk the most is thought to be weakened lower limb muscle strength. For this reason, a technique for easily measuring lower limb muscle strength could be a technology with high demand. However, because the currently available devices that measure lower limb muscle strength are bulky, the devices are difficult to operate without a healthcare professional with specialized knowledge, and widespread use of such devices on a daily basis is difficult.

On the other hand, in the past, standing-up movements or walking movements have been used as indicators to easily evaluate lower limb muscle strength. A significant correlation has been recognized between the movement completion time in a test of standing up 5 times or a test of walking 10 m and lower limb muscle strength. However, because the above movement tests demand exercise that is burdensome for the test subject and are greatly influenced by the skill of the measurer, the above movement tests are problematic from the perspective of safety and reproducibility.

To address such issues, JP-A-2011-78731 for example discloses a physical performance monitoring system that uses a sensing module such as a pressure mat, foot pads, or a force plate and a strength and movement path detection module to estimate exercise/physical performance parameters.

As another example, JP-A-2009-125506 discloses a walking improvement support system that measures the acceleration and direction of the thighs and ankles of a user performing a walking movement and the reaction force from the ground imparted to the soles of the feet, and estimates the muscle balance in the legs on the basis of the measured accelerations, directions, and forces.

However, JP-A-2011-78731 has issues in that the sensing module breaks easily and installing the sensing module takes a large amount of time and effort. Also, with regard to JP-A-2009-125506, in places where space is limited, such as in indoor environments, it is difficult to measure consistent walking, which makes it difficult to evaluate the lower limb muscle strength with high accuracy.

SUMMARY OF THE INVENTION

The present disclosure has been devised to address the above issues, and an object thereof is to provide a technology making it possible to easily evaluate the lower limb muscle strength of a user with high accuracy.

According to an aspect of the present disclosure, there is provided a lower limb muscle strength evaluation method executed by a computer, the method including acquiring an angle of at least one of left and right lower limbs of a user while the user stands up from a sitting state, detecting at least one lower limb parameter from among a first lower limb maximum value indicating the angle when the lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from a point in time when the user begins to stand up until a point in time when the first lower limb maximum value is detected, a second lower limb elapsed time from the point in time when the user begins to stand up until a point in time when the lower limb minimum value is detected, and a third lower limb elapsed time from the point in time when the user begins to stand up until a point in time when the second lower limb maximum value is detected, evaluating a lower limb muscle strength of the user using the at least one lower limb parameter, and outputting an evaluation result.

BRIEF DESCRIPTION OF THE DRAWINGS

FIG. 10 is a diagram illustrating the relationship between estimated values and measured values of lower limb muscle strength evaluation values in a third case of the present embodiment.

DESCRIPTION OF EMBODIMENTS

Figure 1:
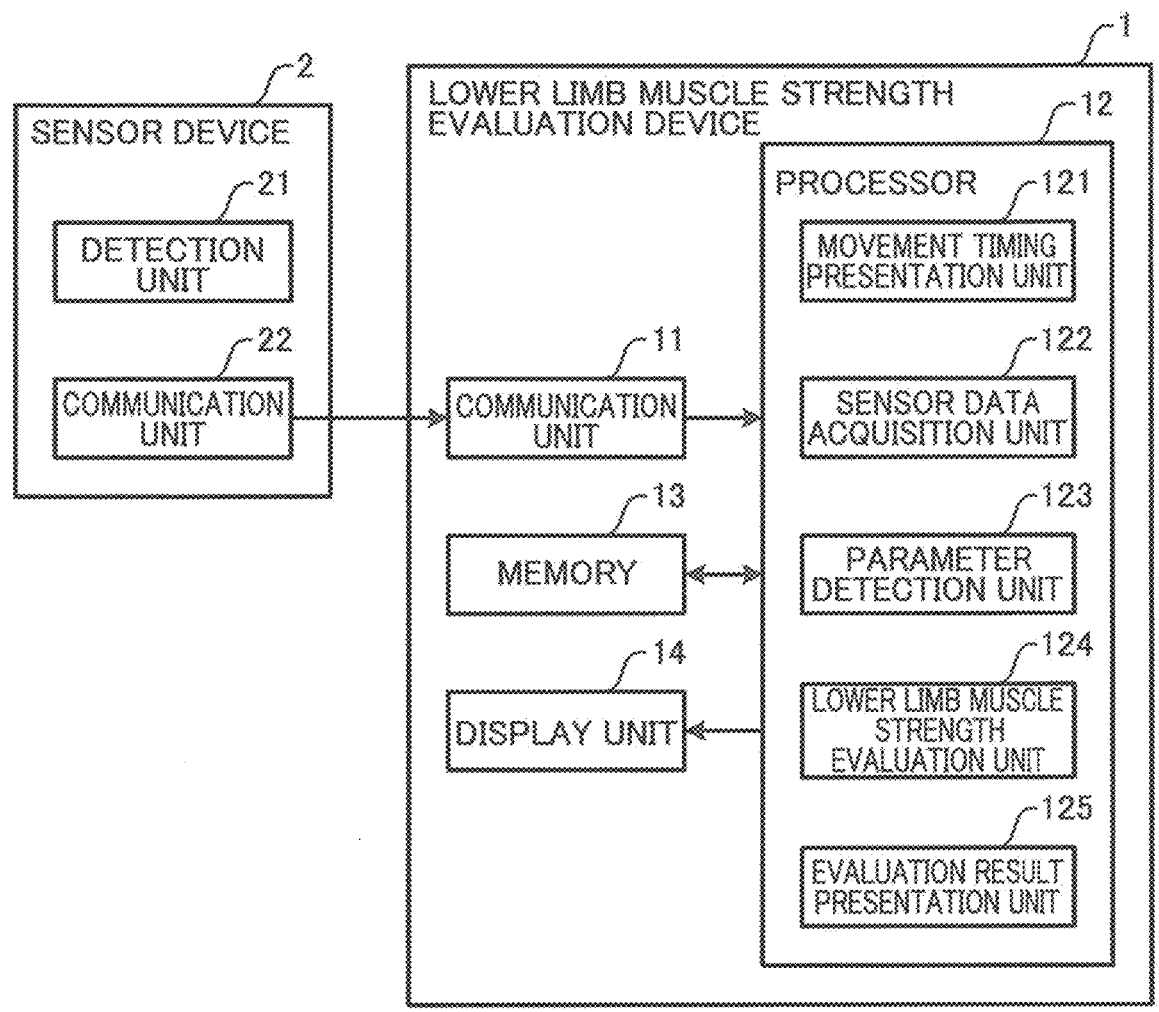
FIG. 1 is a block diagram illustrating a configuration of a lower limb muscle strength evaluation system according to an embodiment of the present disclosure.

Underlying Knowledge Forming Basis of the Present Disclosure

JP-A-2011-78731 above requires a sensing module such as a pressure mat, foot pads, or a force plate. For this reason, JP-A-2011-78731 has issues in that the sensing module breaks easily and installing the sensing module takes a large amount of time and effort.

Also, JP-A-2009-125506 evaluates lower limb muscle strength according to a walking movement. However, in JP-A-2009-125506, a large space is required to consistently measure the walking movement. Therefore, in places where space is limited, such as in indoor environments, it is difficult to measure consistent walking, which makes it difficult to evaluate the lower limb muscle strength with high accuracy.

In order to solve the issues described above, according to an aspect of the present disclosure, there is provided a lower limb muscle strength evaluation method executed by a computer, the method including acquiring an angle of at least one of left and right lower limbs of a user while the user stands up from a sitting state, detecting at least one lower limb parameter from among a first lower limb maximum value indicating the angle when the lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from a point in time when the user begins to stand up until a point in time when the first lower limb maximum value is detected, a second lower limb elapsed time from the point in time when the user begins to stand up until a point in time when the lower limb minimum value is detected, and a third lower limb elapsed time from the point in time when the user begins to stand up until a point in time when the second lower limb maximum value is detected, evaluating a lower limb muscle strength of the user using the at least one lower limb parameter, and outputting an evaluation result.

According to this configuration, a first lower limb maximum value indicating the angle when a lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from the point in time when the user begins to stand up until the point in time when the first lower limb maximum value is detected, a second lower limb elapsed time from the point in time when the user begins to stand up until the point in time when the lower limb minimum value is detected, and a third lower limb elapsed time from the point in time when the user begins to stand up until the point in time when the second lower limb maximum value is detected are the lower limb parameters correlated with the lower limb muscle strength of the user. For this reason, because the lower limb muscle strength of the user is evaluated using at least one lower limb parameter from among a plurality of lower limb parameters correlated with the lower limb muscle strength of the user, the lower limb muscle strength of the user can be evaluated with high accuracy.

Also, because the lower limb parameter described above are used, a movement test with restrictions, such as a movement test of standing up 5 times or a movement test of walking 10 m, does not have to be imposed on the user, and furthermore, a bulky apparatus is unnecessary. Consequently, with this configuration, the lower limb muscle strength of the user can be evaluated easily.

Further, the lower limb muscle strength evaluation method described above may further include acquiring the angle on the basis of sensor data obtained from a sensor worn on at least one of the left and right lower limbs of the user.

According to this configuration, by having the user wear a sensor such as an acceleration sensor or an angular velocity sensor on at least one of the left and right lower limbs, the lower limb muscle strength of the user can be evaluated easily.

Also, in the lower limb muscle strength evaluation method described above, the angle may be acquired using a motion capture system.

According to this configuration, by acquiring the motion of the bone structure of the lower limbs of the user with a motion capture system, the lower limb muscle strength of the user can be evaluated easily.

Further, in the lower limb muscle strength evaluation method described above, at least one lower limb parameter group from among a plurality of first lower limb maximum values, a plurality of lower limb minimum values, a plurality of second lower limb maximum values, a plurality of first lower limb elapsed times, a plurality of second lower limb elapsed times, and a plurality of third lower limb elapsed times may be detected by having the user stand up a plurality of times, and the method may further include calculating at least one lower limb parameter from among an average of the plurality of first lower limb maximum values, an average of the plurality of lower limb minimum values, an average of the plurality of second lower limb maximum values, an average of the plurality of first lower limb elapsed times, an average of the plurality of second lower limb elapsed times, an average of the plurality of third lower limb elapsed times, a standard deviation of the plurality of first lower limb maximum values, a standard deviation of the plurality of lower limb minimum values, a standard deviation of the plurality of second lower limb maximum values, a standard deviation of the plurality of first lower limb elapsed times, a standard deviation of the plurality of second lower limb elapsed times, and a standard deviation of the plurality of third lower limb elapsed times.

According to the configuration, at least one lower limb parameter group from among a plurality of first lower limb maximum values, a plurality of lower limb minimum values, a plurality of second lower limb maximum values, a plurality of first lower limb elapsed times, a plurality of second lower limb elapsed times, and a plurality of third lower limb elapsed times is detected by having the user stand up a plurality of times. Further, at least one lower limb parameter from among an average of the plurality of first lower limb maximum values, an average of the plurality of lower limb minimum values, an average of the plurality of second lower limb maximum values, an average of the plurality of first lower limb elapsed times, an average of the plurality of second lower limb elapsed times, an average of the plurality of third lower limb elapsed times, a standard deviation of the plurality of first lower limb maximum values, a standard deviation of the plurality of lower limb minimum values, a standard deviation of the plurality of second lower limb maximum values, a standard deviation of the plurality of first lower limb elapsed times, a standard deviation of the plurality of second lower limb elapsed times, and a standard deviation of the plurality of third lower limb elapsed times is calculated. Depending on the measurement state of the user, there is a risk that improper sensor data may be acquired. However, by having the user stand up a plurality of times, outliers can be eliminated from the acquired sensor data, and the accuracy of the acquired sensor data can be improved.

Further, in the lower limb muscle strength evaluation method described above, the angles of both the left lower limb and the right lower limb of the user may be acquired while the user stands up from a sitting state, and at least one lower limb parameter from among the first lower limb maximum values corresponding to the left lower limb and the right lower limb, the lower limb minimum values corresponding to the left lower limb and the right lower limb, the second lower limb maximum value corresponding to the left lower limb and the right lower limb, the first lower limb elapsed times corresponding to the left lower limb and the right lower limb, the second lower limb elapsed times corresponding to the left lower limb and the right lower limb, and the third lower limb elapsed times corresponding to the left lower limb and the right lower limb may be detected. Further, the method may further include calculating at least one lower limb parameter from among an average of the first lower limb maximum value corresponding to the left lower limb and the first lower limb maximum value corresponding to the right lower limb, an average of the lower limb minimum value corresponding to the left lower limb and the lower limb minimum value corresponding to the right lower limb, an average of the second lower limb maximum value corresponding to the left lower limb and the second lower limb maximum value corresponding to the right lower limb, an average of the first lower limb elapsed time corresponding to the left lower limb and the first lower limb elapsed time corresponding to the right lower limb, an average of the second lower limb elapsed time corresponding to the left lower limb and the second lower limb elapsed time corresponding to the right lower limb, and an average of the third lower limb elapsed time corresponding to the left lower limb and the third lower limb elapsed time corresponding to the right lower limb.

According to this configuration, in the period from when the user is in a sitting state until the user stands up, the lower limb muscle strength is evaluated on the basis of the motion of both the left lower limb and the right lower limb of the user, and therefore the lower limb muscle strength of the user can be evaluated with higher accuracy.

Further, in the lower limb muscle strength evaluation method described above, the evaluation value of the lower limb muscle strength may be calculated by substituting the at least one detected lower limb parameter into a multiple regression equation that treats the evaluation value of the lower limb muscle strength as a response variable and the at least one lower limb parameter as an explanatory variable.

According to this configuration, by substituting at least one detected lower limb parameter into a multiple regression equation that treats the evaluation value of the lower limb muscle strength as a response variable and the at least one lower limb parameter as an explanatory variable, the evaluation value of the lower limb muscle strength is calculated, and therefore by storing the multiple regression equation in advance, the evaluation value of the lower limb muscle strength can be calculated easily.

Further, the lower limb muscle strength evaluation method described above may further include acquiring an angle of a lumbar of the user while the user stands up from a sitting state, and detecting at least one lumbar parameter from among a first lumbar maximum value indicating the angle when the lumbar is initially inclined the most in a first direction, a lumbar minimum value indicating the angle when the lumbar is inclined the most in a second direction that is opposite the first direction, a second lumbar maximum value indicating the angle when the lumbar is again inclined the most in the first direction, a first lumbar elapsed time from a point in time when the user begins to stand up until a point in time when the first lumbar maximum value is detected, a second lumbar elapsed time from the point in time when the user begins to stand up until a point in time when the lumbar minimum value is detected, and a third lumbar elapsed time from the point in time when the user begins to stand up until a point in time when the second lumbar maximum value is detected, and the lower limb muscle strength of the user may be evaluated using the at least one lower limb parameter and the at least one lumbar parameter.

According to this configuration, in the period from when the user is in a sitting state until the user stands up, the lower limb muscle strength is evaluated on the basis of the motion of the lumbar of the user and the motion of the lower limbs of the user, and therefore the lower limb muscle strength of the user can be evaluated with higher accuracy.

According to another aspect of the present disclosure, there is provided a non-transitory computer-readable recording medium storing a lower limb muscle strength evaluation program causing a computer to execute a process including acquiring an angle of at least one of left and right lower limbs of a user while the user stands up from a sitting state, detecting at least one lower limb parameter from among a first lower limb maximum value indicating the angle when the lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from a point in time when the user begins to stand up until a point in time when the first lower limb maximum value is detected, a second lower limb elapsed time from the point in time when the user begins to stand up until a point in time when the lower limb minimum value is detected, and a third lower limb elapsed time from the point in time when the user begins to stand up until a point in time when the second lower limb maximum value is detected, evaluating a lower limb muscle strength of the user using the at least one lower limb parameter, and outputting an evaluation result.

According to this configuration, a first lower limb maximum value indicating the angle when a lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from the point in time when the user begins to stand up until the point in time when the first lower limb maximum value is detected, a second lower limb elapsed time from the point in time when the user begins to stand up until the point in time when the lower limb minimum value is detected, and a third lower limb elapsed time from the point in time when the user begins to stand up until the point in time when the second lower limb maximum value is detected are the lower limb parameters correlated with the lower limb muscle strength of the user. For this reason, because the lower limb muscle strength of the user is evaluated using at least one lower limb parameter from among a plurality of lower limb parameters correlated with the lower limb muscle strength of the user, the lower limb muscle strength of the user can be evaluated with high accuracy.

Also, because the lower limb parameter described above are used, a movement test with restrictions, such as a movement test of standing up 5 times or a movement test of walking 10 m, does not have to be imposed on the user, and furthermore, a bulky apparatus is unnecessary. Consequently, with this configuration, the lower limb muscle strength of the user can be evaluated easily.

According to another aspect of the present disclosure, there is provided a lower limb muscle strength evaluation device including an acquisition unit that acquires an angle of at least one of left and right lower limbs of a user while the user stands up from a sitting state, a detection unit that detects at least one lower limb parameter from among a first lower limb maximum value indicating the angle when the lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from a point in time when the user begins to stand up until a point in time when the first lower limb maximum value is detected, a second lower limb elapsed time from the point in time when the user begins to stand up until a point in time when the lower limb minimum value is detected, and a third lower limb elapsed time from the point in time when the user begins to stand up until a point in time when the second lower limb maximum value is detected, an evaluation unit that evaluates a lower limb muscle strength of the user using the at least one lower limb parameter, and an output unit that outputs an evaluation result.

According to this configuration, a first lower limb maximum value indicating the angle when a lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from the point in time when the user begins to stand up until the point in time when the first lower limb maximum value is detected, a second lower limb elapsed time from the point in time when the user begins to stand up until the point in time when the lower limb minimum value is detected, and a third lower limb elapsed time from the point in time when the user begins to stand up until the point in time when the second lower limb maximum value is detected are the lower limb parameters correlated with the lower limb muscle strength of the user. For this reason, because the lower limb muscle strength of the user is evaluated using at least one lower limb parameter from among a plurality of lower limb parameters correlated with the lower limb muscle strength of the user, the lower limb muscle strength of the user can be evaluated with high accuracy.

Also, because the lower limb parameter described above are used, a movement test with restrictions, such as a movement test of standing up 5 times or a movement test of walking 10 m, does not have to be imposed on the user, and furthermore, a bulky apparatus is unnecessary. Consequently, with this configuration, the lower limb muscle strength of the user can be evaluated easily.

A lower limb muscle strength evaluation system according to another aspect of the present disclosure is provided with the lower limb muscle strength evaluation device described above, and a sensor that is worn on at least one of the left and right lower limbs of the user and that transmits measured sensor data to the lower limb muscle strength evaluation device.

According to this configuration, by having the user wear a sensor such as an acceleration sensor or an angular velocity sensor on at least one of the left and right lower limbs, the lower limb muscle strength of the user can be evaluated easily.

Hereinafter, an embodiment of the present disclosure will be described with reference to the attached drawings. Note that the following embodiment is merely a specific example of the present disclosure, and does not limit the technical scope of the present disclosure.

Embodiment

Hereinafter, the lower limb muscle strength evaluation system according to the present embodiment will be described on the basis of FIGS. 1 and 2.

Figure 2:
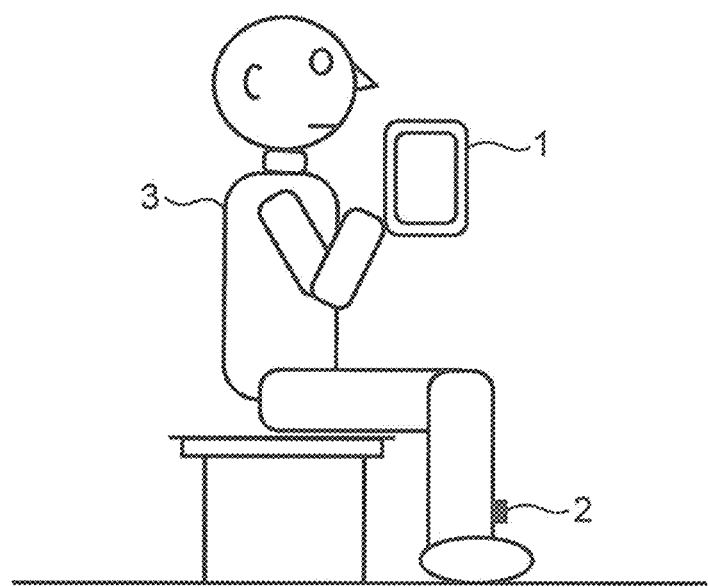
FIG. 2 is a diagram illustrating a state in which a user wears a sensor device in an embodiment of the present disclosure.

FIG. 1 is a block diagram illustrating a configuration of a lower limb muscle strength evaluation system according to an embodiment of the present disclosure. FIG. 2 is a diagram illustrating a state in which a user wears a sensor device in an embodiment of the present disclosure.

The lower limb muscle strength evaluation system according to the present embodiment is provided with a lower limb muscle strength evaluation device 1 and a sensor device 2.

The lower limb muscle strength evaluation device 1 is a terminal device such as a smartphone or a tablet, for example.

The sensor device 2 is worn on at least one of the left and right lower limbs of a user (test subject) 3. In the example illustrated in FIG. 2, the sensor device 2 is being worn on the ankle of the lower right limb of the user 3, for example.

The sensor device 2 is provided with a detection unit 21 and a communication unit 22. The lower limb muscle strength evaluation device 1 and the sensor device 2 are communicably interconnected according to a wireless communication standard such as Bluetooth (registered trademark), for example. Note that the lower limb muscle strength evaluation device 1 and the sensor device 2 may also be communicably interconnected by a wired communication method.

The detection unit 21 detects displacement of the body of the user 3.

First, details about the detection unit 21 will be described.

The detection unit 21 detects body movement of the user 3 performing a standing-up movement. For example, a known attitude sensor can be adopted as the detection unit 21.

The detection unit 21 detects the angular velocity of the body of the user 3, and outputs an angular velocity signal. The attitude sensor is typically provided with components such as a 3-axis acceleration sensor, a 3-axis gyro sensor (angular velocity sensor), and a 3-axis geomagnetic sensor (angular displacement measurement), thereby making it possible to measure the accelerations and rotational angles in the up, down, left, right, forward, and back directions of the body of the user 3 with a single sensor.

The detection unit 21 may also be an angular velocity sensor attached to a terminal device such as a smartphone or tablet, for example. The detection unit 21 does not have to output raw data directly, and may also output data that has been processed to correct for offset and sensitivity, for example. The detection unit 21 may also perform a correction process that compensates for temperature using a temperature measured by a temperature sensor separately built into the sensor device 2.

The detection unit 21 detects the angular velocity about the rotational axis in the horizontal left-and-right direction of the user 3 when the user 3 stands up.

The detection unit 21 may also be an acceleration sensor. In this case, the detection unit 21 detects the acceleration acting in the vertical direction or the horizontal front-and-back direction. Additionally, the detection unit 21 may also use a combined acceleration obtained by combining the accelerations along three axes.

Note that the installation position of the sensor device 2 is not strictly limited. The sensor device 2 is preferably worn by being wrapped around the ankle or thigh area with a belt or the like, and more specifically, is preferably worn on a part of the leg that makes it possible to capture the motions of the lower limb while the user is standing up. The sensor device 2 is preferably worn in the area between the knee and the ankle of the user 3. In the case where the sensor device 2 is worn on the ankle, the sensor device 2 may be worn on the ankle of only one leg of the user 3. In the present embodiment, the sensor device 2 is worn on the front portion of the ankle of one leg of the user 3. Note that the sensor device 2 may also be worn on the body of the user 3 by being stuck onto a shoe or a piece of clothing (such as pants or socks) worn by the user 3, by being embedded into a shoe or a piece of clothing, or by being affixed to a shoe or a piece of clothing with a clip or the like. In the case where the sensor device 2 is attached to a position on the front portion of the ankle, properties such as the acceleration and rotational angle can be measured in a state of little disturbance (fluctuations caused by movements other than standing up). With this arrangement, an advantage of being able to accurately measure the acceleration or rotational angle of the body of the user 3 is obtained.

Also, for example, the detection unit 21 measures a body movement signal at a predetermined sampling frequency (for example, 100 Hz). The sampling frequency for measuring body movement is not strictly limited insofar as the frequency is sufficient to track the speed of body movement, but is preferably in the range from 10 Hz to 1,000 Hz, for example.

The communication unit 22 transmits sensor data detected by the detection unit 21 to the lower limb muscle strength evaluation device 1 by a wireless communication method of a wired communication method.

The lower limb muscle strength evaluation device 1 is provided with a communication unit 11, a processor 12, memory 13, and a display unit 14.

The processor 12 is a central processing unit (CPU) for example, and is provided with a movement timing presentation unit 121, a sensor data acquisition unit 122, a parameter detection unit 123, a lower limb muscle strength evaluation unit 124, and an evaluation result presentation unit 125.

The memory 13 is a storage device capable of storing various information, such as random access memory (RAM), a hard disk drive (HDD), a solid-state drive (SSD), or flash memory, for example.

The movement timing presentation unit 121 presents a timing when the test subject (user 3) is to perform a standing-up movement. The movement timing presentation unit 121 displays the timing when the user 3 is to begin the standing-up movement on the display unit 14. Note that the movement timing presentation unit 121 may also present the timing when to perform the standing-up movement with voice or a buzzer sound output from a speaker. Additionally, the movement timing presentation unit 121 may also present the timing when to perform the standing-up movement with a light emitter such as a light-emitting diode (LED). Note that the movement timing presentation unit 121 may include at least one of a function of presenting information visually and a function of presenting information aurally, for example.

As an example of a pattern by which the movement timing presentation unit 121 presents the timing of the standing-up movement, first, the movement timing presentation unit 121 notifies the user 3 by voice guidance to stand up at the same timing as a buzzer sound. Thereafter, the movement timing presentation unit 121 outputs the buzzer sound when 0.5 seconds have elapsed since the notification by voice guidance. With this arrangement, the movement timing presentation unit 121 may present the timing of the standing-up movement. Note that in the case of causing the user 3 to perform the standing-up movement a plurality of times, the movement timing presentation unit 121 may output the buzzer sound a plurality of times. In this case, the timings when to output the buzzer sound are preset. The buzzer sound is output at a preset time interval. Specifically, in the case of standing up at a timing of once every 1 to 3 seconds, the time interval for outputting the buzzer sound may be set within a range from 0.33 Hz to 1 Hz cycles. Additionally, the movement timing presentation unit 121 may not only present a timing when to stand up from a seated state, but also present a timing when to sit down from a standing state.

The timing for standing up may be presented one time, but is preferably presented 3 to 5 times, for example.

The communication unit 11 receives sensor data transmitted by the sensor device 2. The communication unit 11 outputs the received sensor data to the processor 12. A wireless communication method or a wired communication method can be applied as the method of receiving the sensor data. In this case, the communication unit 11 receives the sensor data using a communication method that allows the sensor data to be received.

The sensor data acquisition unit 122 acquires the angle of at least one of the left and right lower limbs of the user 3 while the user 3 stands up from a sitting state. The sensor data acquisition unit 122 acquires the angle on the basis of sensor data obtained from the sensor device 2 worn on at least one of the left and right lower limbs of the user 3.

The sensor data acquisition unit 122 acquires a signal from the detection unit 21 and performs data processing with a low-pass filter or the like to remove noise. Note that the cutoff frequency of the low-pass filter is preferably from 4 Hz to 20 Hz. Also, in the case where the detection unit 21 is a 1-axis angular velocity sensor, the sensor data acquisition unit 122 may also convert an angular velocity signal from the 1-axis angular velocity sensor to an angle by taking the first-order integral with respect to time. However, simply integrating the angular velocity may cause drift. Accordingly, the sensor data acquisition unit 122 may calculate a relative angle by calculating a regression curve with respect to the angular velocity integration result, and subtracting the value of the calculated regression curve from the integration result. The sensor data acquisition unit 122 may also suppress drift by using a high-pass filter.

Also, in the case where the detection unit 21 is an acceleration sensor, the sensor data acquisition unit 122 may convert the detected acceleration into an angle about the rotational axis in the horizontal left-and-right direction of the user 3 when the user 3 stands up. The sensor data acquisition unit 122 converts the acceleration acting in the vertical direction or the horizontal front-and-back direction of the acceleration sensor into an angle.

$$\text{Angle} = \arccos(a/g) \qquad (1)$$

In Formula (1) above, a is the acceleration and g is the gravitational acceleration. The sensor data acquisition unit 122 may calculate an angle from the acceleration signal on the basis of Formula (1) above.

Note that the detection unit 21 of the sensor device 2 may convert the detected angular velocity into an angle by integrating over time, and the sensor data acquisition unit 122 may acquire the angle converted by the detection unit 21.

The parameter detection unit 123 detects lower limb parameters for evaluating the lower limb muscle strength.

Figure 3:
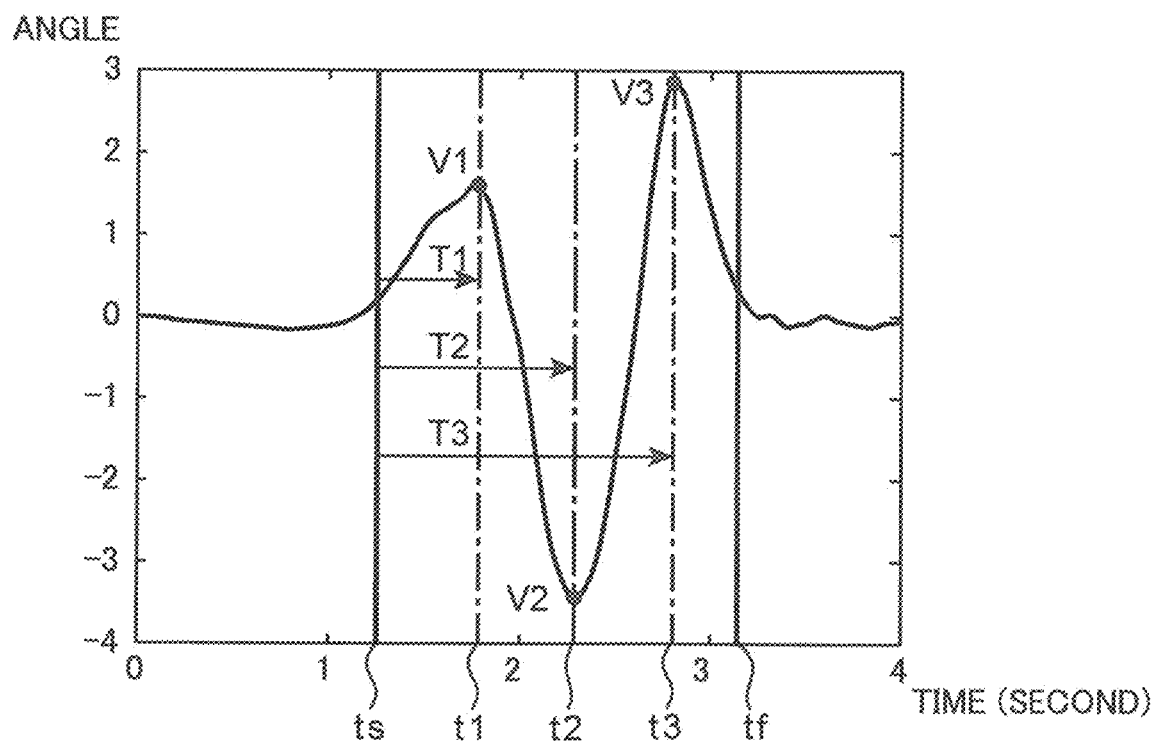
FIG. 3 is a graph for explaining lower limb parameters in the present embodiment.
Figure 4:
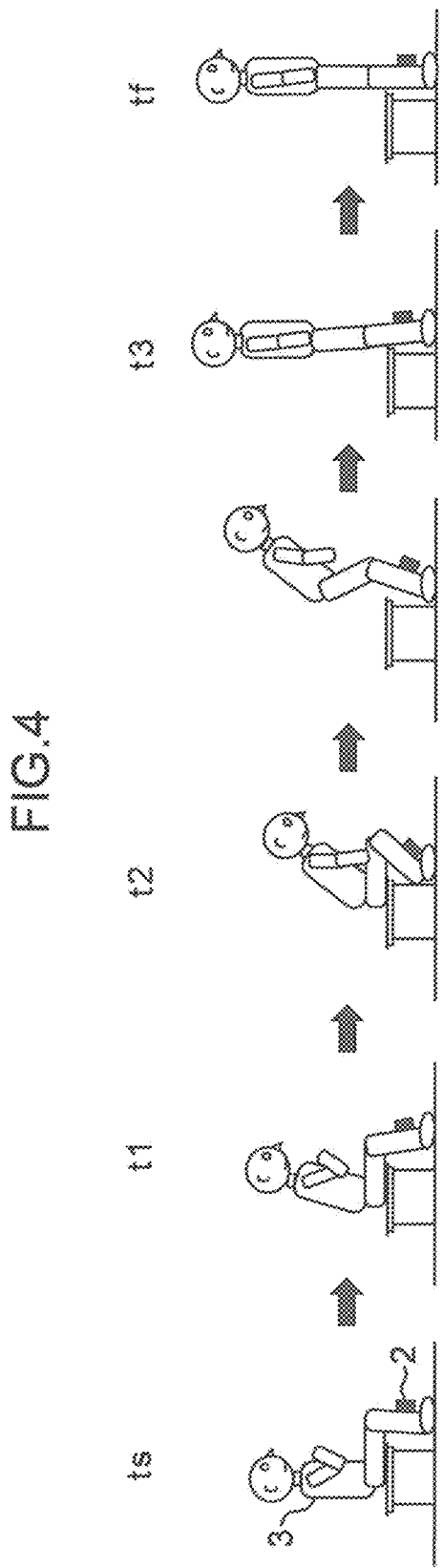
FIG. 4 is a diagram illustrating a standing-up movement by a user in the present embodiment.

FIG. 3 is a graph for explaining lower limb parameters in the present embodiment. In FIG. 3, the horizontal axis represents the angle of the lower limb, and the horizontal axis represents time. FIG. 4 is a diagram illustrating a standing-up movement by a user in the present embodiment.

The parameter detection unit 123 detects at least one lower limb parameter of a first lower limb maximum value V1 indicating the angle when a lower limb is initially inclined the most in a first direction, a lower limb minimum value V2 indicating the angle when the lower limb is inclined the most in a second direction that is opposite the first direction, a second lower limb maximum value V3 indicating the angle when the lower limb is again inclined the most in the first direction, a first lower limb elapsed time T1 from the point in time when the user 3 begins to stand up until the point in time when the first lower limb maximum value V1 is detected, a second lower limb elapsed time T2 from the point in time when the user 3 begins to stand up until the point in time when the lower limb minimum value V2 is detected, or a third lower limb elapsed time T3 from the point in time when the user 3 begins to stand up until the point in time when the second lower limb maximum value V3 is detected.

In FIGS. 3 and 4, a time ts indicates the point in time when the user 3 begins to stand up, a time t1 indicates the point in time when a first lower limb maximum value V1 is detected, a time t2 indicates the point in time when a lower limb minimum value V2 is detected, a time t3 indicates the point in time when a second lower limb maximum value V3 is detected, and a time tf indicates the point in time when the user 3 finishes standing up.

In the case where the lower limb of the user 3 is parallel to the vertical direction, the angle of the lower limb is 0 degrees. The angle is expressed with a positive sign when the lower limb is inclined about the knee toward the front of the user 3 from the vertical direction, and with a negative sign when the lower limb is inclined about the knee toward the back of the user 3 from the vertical direction.

At this point, the standing-up movement by the user 3 will be described.

As illustrated in FIG. 4, the user 3 stands up from a state of sitting in a chair. First, at the point in time when standing up begins (time ts), the lower limb of the user 3 is parallel to the vertical direction. At this time, the angle of the lower limb is 0 degrees.

Next, at the time t1, the user 3 flexes the ankle with plantar flexion. Accordingly, the lower limb of the user 3 is inclined forward about the knee, and the first lower limb maximum value V1 is detected.

Next, at the time t2, the user 3 flexes the ankle with dorsiflexion. Accordingly, the lower limb of the user 3 is inclined backward about the knee, and the lower limb minimum value V2 is detected.

Next, the user 3 raises his or her buttocks from the chair and begins to extend the knee.

Next, at the time t3, the user 3 extends the knee. At this time, the lower limb of the user 3 is inclined forward about the knee, and the second lower limb maximum value V3 is detected.

Next, at the time tf, the user 3 finishes the standing-up movement. At this time, the lower limb of the user 3 is parallel to the vertical direction, and the angle of the lower limb is 0 degrees.

The parameter detection unit 123 detects lower limb parameters, including at least one of the first lower limb maximum value V1, the lower limb minimum value V2, and the second lower limb maximum value V3 of the standing-up angle of the user 3 on which the sensor device 2 is worn, a first lower limb elapsed time T1, a second lower limb elapsed time T2, and a third lower limb elapsed time T3, on the basis of signals acquired by the sensor data acquisition unit 122. The parameter detection unit may also detect lower limb parameters, including at least one of the first lower limb maximum value V1, the lower limb minimum value V2, the second lower limb maximum value V3, the first lower limb elapsed time T1, the second lower limb elapsed time T2, and the third lower limb elapsed time T3, on the basis of angles converted from acceleration signals obtained by the detection unit 21.

For example, the parameter detection unit 123 may treat a point in time when a signal exceeds a threshold (the point in time when standing up from the sitting state begins) as a reference, and calculate the time taken until the point in time when the signal next exceeds the threshold (standing state) as a standing-up interval. Also, for example, the parameter detection unit 123 may calculate the period during which the sum of the angular velocity and the acceleration exceeds a threshold as the standing-up interval. Note that the threshold may be 5% of a maximum value. In FIG. 3, the period from the time ts to the time tf is the standing-up interval.

When the standing-up interval is treated as an interval from 0% to 100%, the parameter detection unit 123 may detect the maximum value of the signal from 0% to 50% of the standing-up interval as the first lower limb maximum value V1, and detect the maximum value of the signal from 51% to 100% of the standing-up interval as the second lower limb maximum value V3. Additionally, the parameter detection unit 123 may also detect the minimum value of the signal from 0% to 100% of the standing-up interval as the lower limb minimum value V2. Furthermore, the parameter detection unit 123 detects the time from the point in time when standing up begins until the first lower limb maximum value V1 is detected as the first lower limb elapsed time T1, detects the time from the point in time when standing up begins until the lower limb minimum value V2 is detected as the second lower limb elapsed time T2, and detect the time from the point in time when standing up begins until the second lower limb maximum value V3 is detected as the third lower limb elapsed time T3.

The lower limb muscle strength evaluation unit 124 evaluates the lower limb muscle strength of the user 3 using at least one of the lower limb parameters detected by the parameter detection unit 123. The lower limb muscle strength evaluation unit 124 calculates an evaluation value of the lower limb muscle strength by substituting at least one detected lower limb parameter into a multiple regression equation that treats the evaluation value of the lower limb muscle strength as a response variable and the at least one lower limb parameter as an explanatory variable. The evaluation value of the lower limb muscle strength is the value obtained by dividing a lower limb muscle strength value by bodyweight.

The memory 13 stores the multiple regression equation for quantifying the lower limb muscle strength of the user 3 on the basis of the lower limb parameters detected by the parameter detection unit 123. The multiple regression equation is derived by causing dozens of test subjects having different lower limb muscle strength values to perform standing-up movements in advance, acquiring evaluation values of the lower limb muscle strength, and calculating a multiple regression line using at least one lower limb parameter detected by the parameter detection unit 123 and the acquired evaluation values of the lower limb muscle strength.

The lower limb muscle strength evaluation unit 124 calculates the value obtained by dividing a lower limb muscle strength value by bodyweight as an evaluation value of the lower limb muscle strength. The lower limb muscle strength evaluation unit 124 may also output the evaluation value of the lower limb muscle strength as a value indicating the danger of a falling risk. In this case, for example, the lower limb muscle strength evaluation unit 124 may evaluate the danger of falling as high in the case where the evaluation value of the lower limb muscle strength is 0.4 or less. The lower limb muscle strength evaluation unit 124 may also evaluate the evaluation value of the lower limb muscle strength in increments of 0.2. In this case, for example, the lower limb muscle strength evaluation unit 124 evaluates the danger of falling as extremely high if the evaluation value of the lower limb muscle strength is 0.4 or less, high if the evaluation value of the lower limb muscle strength is greater than 0.4 and 0.6 or less, somewhat high if the evaluation value of the lower limb muscle strength is greater than 0.6 and 0.8 or less, and low if the evaluation value of the lower limb muscle strength is greater than 0.8. For example, in the case where the evaluation value of the lower limb muscle strength is 0.9, the lower limb muscle strength evaluation unit 124 evaluates the danger of falling as low. Further, in the case where the evaluation value of the lower limb muscle strength is 0.5, the lower limb muscle strength evaluation unit 124 evaluates the danger of falling as high.

Note that the lower limb muscle strength evaluation unit 124 may calculate the lower limb muscle strength value by substituting at least one detected lower limb parameter into a multiple regression equation that treats the lower limb muscle strength value as a response variable and the at least one lower limb parameter as an explanatory variable. In addition, the lower limb muscle strength evaluation unit 124 may calculate the lower limb muscle strength value only, the evaluation value of the lower limb muscle strength only, or both the lower limb muscle strength value and the evaluation value of the lower limb muscle strength.

The lower limb muscle strength evaluation unit 124 may store the calculated lower limb muscle strength value or the evaluation value of the lower limb muscle strength in the memory 13. The memory 13 may also store evaluation messages associated with lower limb muscle strength values or evaluation values of the lower limb muscle strength in advance. For example, an evaluation message stating "The falling risk is somewhat high. Please try to exercise more." is associated with an evaluation indicating that the falling risk is somewhat high. Also, an evaluation message stating "The falling risk is low. Please maintain your current exercise routine." is associated with an evaluation indicating that the falling risk is low.

The memory 13 may store at least one of the lower limb muscle strength value or the evaluation value of the lower limb muscle strength calculated by the lower limb muscle strength evaluation unit 124. Additionally, the memory 13 may also store evaluation messages.

The evaluation result presentation unit 125 outputs an evaluation result evaluated by the lower limb muscle strength evaluation unit 124 to the display unit 14. The evaluation result is at least one of the lower limb muscle strength value and evaluation value of the lower limb muscle strength calculated by the lower limb muscle strength evaluation unit 124, and the evaluation message.

The display unit 14 displays an evaluation result indicating at least one of the lower limb muscle strength value, the evaluation value of the lower limb muscle strength, and the evaluation message output from the evaluation result presentation unit 125. For example, the display unit 14 is a liquid crystal display panel or a light-emitting device, and is disposed in a position allowing the user 3 to view an image easily. The display unit 14 may also be a wristwatch-style liquid crystal display, for example. With this arrangement, the user 3 is able to perform the standing-up movement while looking at the wristwatch-style liquid crystal display worn on the arm.

The display unit 14 may also display a trend of the evaluation value of the lower limb muscle strength as a graph to compare the currently calculated evaluation value of the lower limb muscle strength to previous evaluation values of the lower limb muscle strength. Note that past evaluation values of the lower limb muscle strength are read out from the memory 13.

Note that in the case where the lower limb muscle strength evaluation device 1 is worn in a difficult-to-see position, such as on the part of the leg for example, the lower limb muscle strength evaluation device 1 may be provided with a speaker instead of the display unit 14. The speaker may output the evaluation result by the lower limb muscle strength evaluation unit 124 using a buzzer sound or voice. For example, in the case where the falling risk is evaluated as high, the speaker may output a buzzer sound.

Also, in the present embodiment, the lower limb muscle strength evaluation system is provided with the lower limb muscle strength evaluation device 1 and the sensor device 2, but the present disclosure is not strictly limited thereto. The lower limb muscle strength evaluation system may also be provided with the lower limb muscle strength evaluation device 1 only. In this case, the lower limb muscle strength evaluation device 1 may also be provided with the detection unit 21 of the sensor device 2, and the lower limb muscle strength evaluation device 1 may be worn directly on a lower limb of the user 3.

Additionally, a server communicably connected to the lower limb muscle strength evaluation device 1 over a network may be provided with some or all of the sensor data acquisition unit 122, the parameter detection unit 123, the lower limb muscle strength evaluation unit 124, and the evaluation result presentation unit 125.

Figure 5:
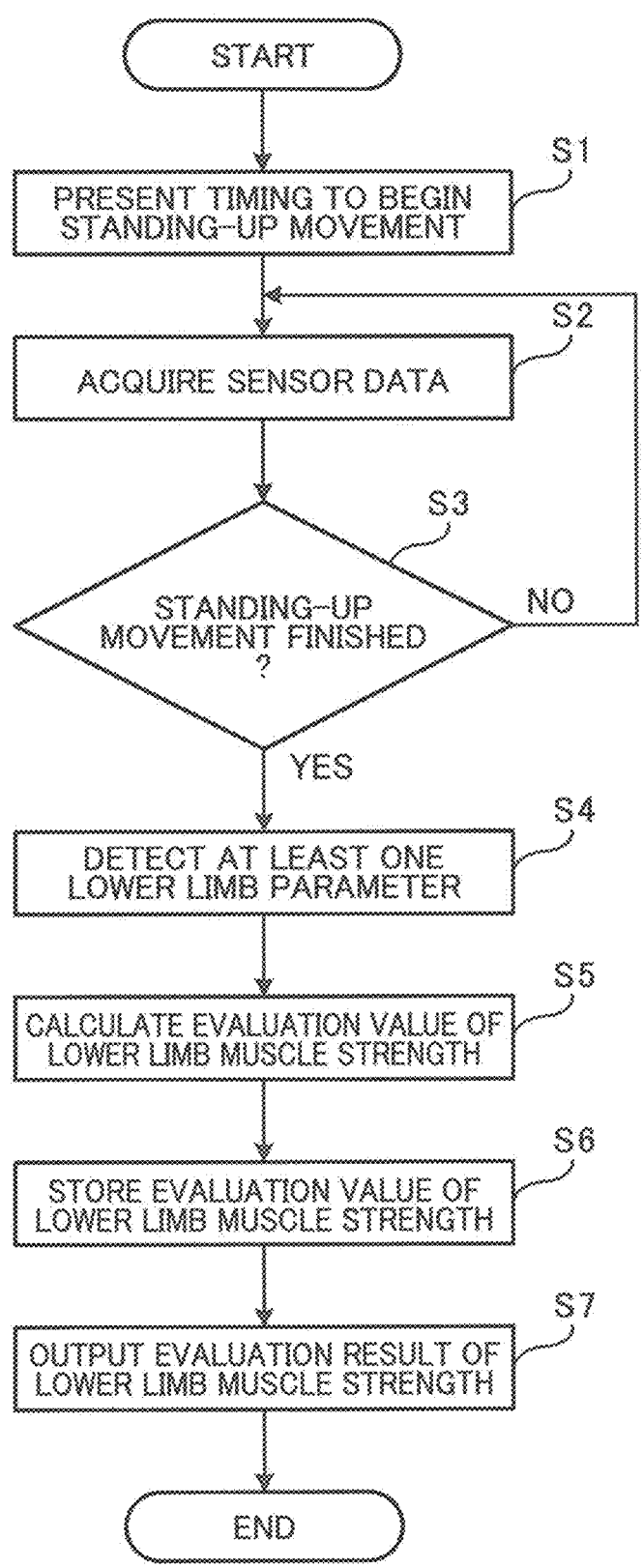
FIG. 5 is a flowchart for explaining a lower limb muscle strength evaluation process utilizing a standing-up movement in the present embodiment.

Next, FIG. 5 will be referenced to describe a lower limb muscle strength evaluation process according to the present embodiment.

FIG. 5 is a flowchart for explaining a lower limb muscle strength evaluation process utilizing a standing-up movement in the present embodiment. The flowchart illustrated in FIG. 5 illustrates a procedure for calculating and evaluating the lower limb muscle strength using the lower limb muscle strength evaluation device 1.

The test subject (user 3) works the sensor device 2 on his or her ankle. Additionally, after putting on the sensor device 2, the test subject sets a power switch (not illustrated) of the sensor device 2 to the ON state. Note that when the power switch is set to the ON state, the lower limb muscle strength evaluation device 1 or the sensor device 2 may also accept the input of a number of times to stand up. In the flowchart illustrated in FIG. 5, the number of times to stand up is 1 time. Also, the test subject sets a power switch (not illustrated) of the lower limb muscle strength evaluation device 1 to the ON state.

First, the movement timing presentation unit 121 presents the timing to begin the standing-up movement on the display unit 14 (step S1).

Next, the sensor data acquisition unit 122 acquires sensor data indicating the acceleration or the angular velocity detected by the sensor device 2 (step S2). At this time, the detection unit 21 of the sensor device 2 detects the acceleration or the angular velocity of the lower limb of the user 3. The communication unit 22 transmits the acceleration or the angular velocity detected by the detection unit 21 as sensor data to the lower limb muscle strength evaluation device 1. The communication unit 11 of the lower limb muscle strength evaluation device 1 receives the sensor data transmitted by the sensor device 2, and outputs the received sensor data to the sensor data acquisition unit 122.

The sensor data acquisition unit 122 converts the sensor data acquired from the sensor device 2 into an angle. In the case where the sensor data is angular velocity, the sensor data acquisition unit 122 converts the angular velocity into an angle by integrating the angular velocity. The angle is a rotational angle about the rotational axis in the horizontal left-and-right direction, the angle changing according to the plantar flexion or dorsiflexion of the ankle.

After that, the test subject stands up from a seated state, and changes from a sitting posture to a standing posture. It is desirable for the height of the chair to be lower than the knee joint. Also, the standing-up movement may be a movement of changing to a standing posture from a posture of squatting on the floor rather than from a posture of sitting in a chair.

While the test subject is performing the standing-up movement, the sensor data acquisition unit 122 acquires the acceleration or the angular velocity from the sensor device 2. Note that the sensor data acquisition unit 122 acquires the detection results, namely the acceleration or the angular velocity, as discrete values associated with predetermined sampling times.

Next, the parameter detection unit 123 determines whether or not the standing-up movement is finished (step S3). At this point, in the case of determining that the standing-up movement is not finished (step S3, No), the process returns to step S2.

On the other hand, in the case of determining that the standing-up movement is finished (step S3, Yes), the parameter detection unit 123 detects at least one lower limb parameter from among a plurality of lower limb parameters (step S4). The plurality of lower limb parameters are a first lower limb maximum value V1 indicating the angle when a lower limb is initially inclined the most in a first direction, a lower limb minimum value V2 indicating the angle when the lower limb is inclined the most in a second direction that is opposite the first direction, a second lower limb maximum value V3 indicating the angle when the lower limb is again inclined the most in the first direction, a first lower limb elapsed time T1 from the point in time when the user 3 begins to stand up until the point in time when the first lower limb maximum value V1 is detected, a second lower limb elapsed time T2 from the point in time when the user 3 begins to stand up until the point in time when the lower limb minimum value V2 is detected, and a third lower limb elapsed time from T3 the point in time when the user 3 begins to stand up until the point in time when the second lower limb maximum value V3 is detected.

The parameter detection unit 123 may detect all of the above plurality of lower limb parameters, or only the lower limb parameter(s) to use for evaluating the lower limb muscle strength.

When the standing-up interval is treated as an interval from 0% to 100%, the parameter detection unit 123 detects, from the plantar flexion angle and dorsiflexion angle of the ankle, the maximum value of the angle from 0% to 50% of the standing-up interval as the first lower limb maximum value V1, and detects the maximum value of the angle from 51% to 100% of the standing-up interval as the second lower limb maximum value V3. Additionally, the parameter detection unit 123 detects the minimum value of the angle from 0% to 100% of the standing-up interval as the lower limb minimum value V2. Furthermore, the parameter detection unit 123 detects the time from the point in time when standing up begins until the first lower limb maximum value V1 is detected as the first lower limb elapsed time T1, detects the time from the point in time when standing up begins until the lower limb minimum value is detected as the second lower limb elapsed time T2, and detects the time from the point in time when standing up begins until the second lower limb maximum value V3 is detected as the third lower limb elapsed time T3.

Next, the lower limb muscle strength evaluation unit 124 calculates the evaluation value of the lower limb muscle strength of the user 3 using at least one of the lower limb parameters detected by the parameter detection unit 123 (step S5). The lower limb muscle strength evaluation unit 124 calculates an evaluation value of the lower limb muscle strength by substituting the at least one lower limb parameter into a preconstructed lower limb muscle strength evaluation model (multiple regression equation). The evaluation value of the lower limb muscle strength is the value obtained by dividing a lower limb muscle strength value by bodyweight. Note that the lower limb muscle strength evaluation unit 124 may calculate the lower limb muscle strength value using at least one of the lower limb parameters detected by the parameter detection unit 123. The lower limb muscle strength evaluation unit 124 calculates at least one of the lower limb muscle strength value or the evaluation value of the lower limb muscle strength.

Next, the lower limb muscle strength evaluation unit 124 stores the evaluation value of the lower limb muscle strength in the memory 13 (step S6). Note that the lower limb muscle strength evaluation unit 124 may store the calculated lower limb muscle strength value in the memory 13. The lower limb muscle strength evaluation unit 124 stores at least one of the calculated lower limb muscle strength value or the calculated evaluation value of the lower limb muscle strength in the memory 13.

Next, the evaluation result presentation unit 125 outputs the evaluation result of the lower limb muscle strength including the evaluation value of the lower limb muscle strength calculated by the lower limb muscle strength evaluation unit 124 to the display unit 14 (step S7). Note that the evaluation result presentation unit 125 may also output, to the display unit 14, an evaluation result of the lower limb muscle strength including not only the evaluation value of the lower limb muscle strength but also an evaluation message associated with the evaluation value. The display unit 14 displays the evaluation result of the lower limb muscle strength output from the evaluation result presentation unit 125.

Figure 6:
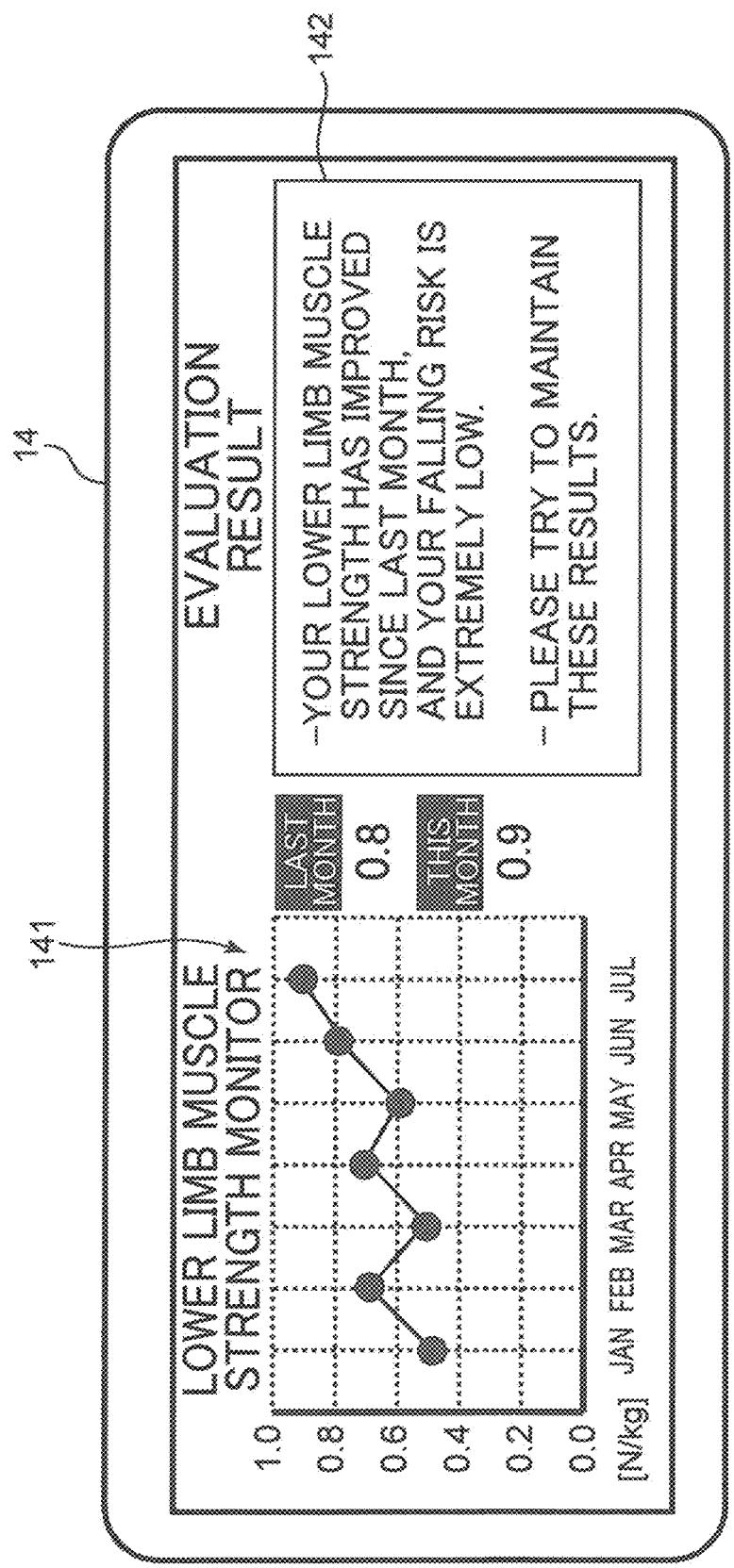
FIG. 6 is a diagram illustrating an example of an evaluation result screen displayed in the present embodiment.

FIG. 6 is a diagram illustrating an example of an evaluation result screen displayed in the present embodiment.

The display unit 14 displays the evaluation result screen illustrated in FIG. 6. The evaluation result screen includes a lower limb muscle strength monitor 141 indicating previous evaluation values of the lower limb muscle strength and the current evaluation value of the lower limb muscle strength, and an evaluation message 142. On the lower limb muscle strength monitor 141 in FIG. 6, an evaluation of the lower limb muscle strength has been performed once a month, and the evaluation values of the lower limb muscle strength for the past six months as well as the evaluation value of the lower limb muscle strength for the current month are displayed.

Also, the evaluation message 142 is displayed, stating "Your lower limb muscle strength has improved since last month, and your falling risk is extremely low. Please try to maintain these results." In the case where the evaluation value of the lower limb muscle strength for the current month is higher than the evaluation value of the lower limb muscle strength for the last month, and the evaluation value of the lower limb muscle strength for the current month is greater than 0.8, the evaluation result presentation unit 125 reads out the evaluation message 142 illustrated in FIG. 6 from the memory 13, and outputs the evaluation message 142 to the display unit 14.

Note that in the present embodiment, the current evaluation value of the lower limb muscle strength is displayed together with past evaluation values of the lower limb muscle strength, but the present disclosure is not strictly limited thereto, and the current evaluation value of the lower limb muscle strength may also be displayed alone. In this case, the lower limb muscle strength evaluation unit 124 does not have to store the evaluation value of the lower limb muscle strength in the memory 13.

According to a process like the above, the lower limb muscle strength evaluation device 1 is capable of easily evaluating the lower limb muscle strength of the test subject from a standing-up movement performed by the test subject. Specifically, the falling risk is increased in cases where the evaluation value of the lower limb muscle strength is 0.4 or less. For this reason, by using the evaluation result of the lower limb muscle strength, the falling risk due to a reason other than a decrease in lower limb muscle strength can be estimated easily.

Additionally, the lower limb muscle strength evaluation device 1 can evaluate the lower limb muscle strength easily with a relatively simple configuration like the above, and therefore can be introduced easily even into small-scale hospitals or nursing homes. Furthermore, even elderly persons can be test subjects easily. With this arrangement, the state of the lower limb muscle strength of elderly persons can be more ascertained, thereby making it possible to establish a rehabilitation plan early and prevent problems such as broken bones associated with a decrease in lower limb muscle strength.

As described above, a first lower limb maximum value indicating the angle when a lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from the point in time when the user 3 begins to stand up until the point in time when the first lower limb maximum value is detected, a second lower limb elapsed time from the point in time when the user 3 begins to stand up until the point in time when the lower limb minimum value is detected, and a third lower limb elapsed time from the point in time when the user 3 begins to stand up until the point in time when the second lower limb maximum value is detected are the lower limb parameters correlated with the lower limb muscle strength of the user 3. For this reason, because the lower limb muscle strength of the user 3 is evaluated using at least one lower limb parameter from among a plurality of lower limb parameters correlated with the lower limb muscle strength of the user 3, the lower limb muscle strength of the user 3 can be evaluated with high accuracy.

Also, because the lower limb parameter described above are used, a movement test with restrictions, such as a movement test of standing up 5 times or a movement test of walking 10 m, does not have to be imposed on the user 3, and furthermore, a bulky apparatus is unnecessary. Consequently, with this configuration, the lower limb muscle strength of the user 3 can be evaluated easily.

Note that although the standing-up movement is performed one time in the present embodiment, the present disclosure is not strictly limited thereto, and the standing-up movement may also be performed multiple times.

In this case, the parameter detection unit 123 may detect at least one lower limb parameter group from among a plurality of first lower limb maximum values, a plurality of lower limb minimum values, a plurality of second lower limb maximum values, a plurality of first lower limb elapsed times, a plurality of second lower limb elapsed times, and a plurality of third lower limb elapsed times, by having the user 3 stand up a plurality of times. Further, the parameter detection unit 123 may calculate at least one lower limb parameter from among an average of the plurality of first lower limb maximum values, an average of the plurality of lower limb minimum values, an average of the plurality of second lower limb maximum values, an average of the plurality of first lower limb elapsed times, an average of the plurality of second lower limb elapsed times, an average of the plurality of third lower limb elapsed times, a standard deviation of the plurality of first lower limb maximum values, a standard deviation of the plurality of lower limb minimum values, a standard deviation of the plurality of second lower limb maximum values, a standard deviation of the plurality of first lower limb elapsed times, a standard deviation of the plurality of second lower limb elapsed times, and a standard deviation of the plurality of third lower limb elapsed times.

Figure 7:
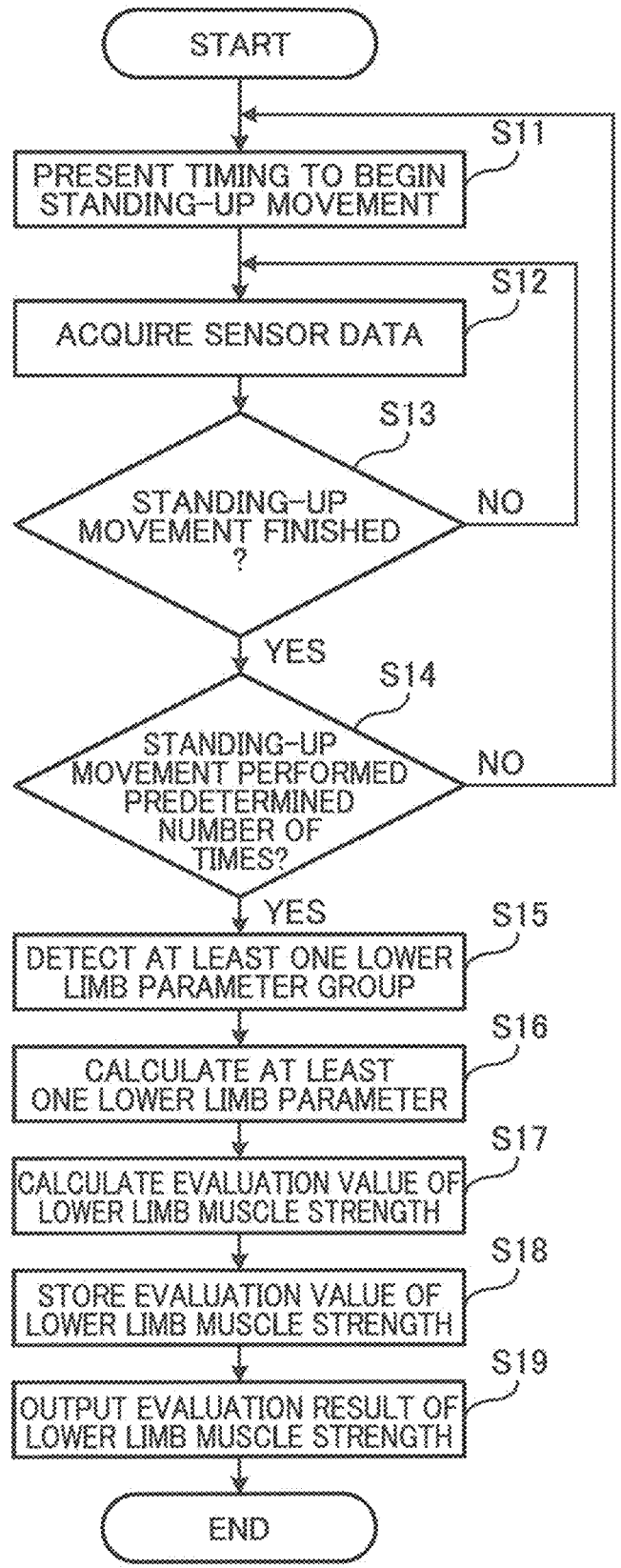
FIG. 7 is a flowchart for explaining a lower limb muscle strength evaluation process utilizing a plurality of standing-up movements in a modification of the present embodiment.

FIG. 7 is a flowchart for explaining a lower limb muscle strength evaluation process utilizing a plurality of standing-up movements in a modification of the present embodiment.

The process from steps S11 to S13 illustrated in FIG. 7 is the same as the process from steps S1 to S3 illustrated in FIG. 5, and therefore a description is omitted.

In the case of determining that the standing-up movement is finished (step S13, Yes), the parameter detection unit 123 determines whether or not the standing-up movement has been performed a predetermined number of times (step S14). The predetermined number of times is three times, for example. The predetermined number of times may be predetermined or set by the user 3. In the case where the lower limb muscle strength is evaluated from a single standing-up movement, improper measurement data may be acquired depending on the measurement state of the test subject. For this reason, by causing the test subject to perform the standing-up movement approximately three to five times and eliminating outliers from the acquired measurement data, for example, the accuracy of the acquired measurement data can be improved.

At this point, in the case of determining that the standing-up movement has not been performed the predetermined number of times (step S14, No), the process returns to step S11, and the timing to begin the standing-up movement is presented.

On the other hand, in the case of determining that the standing-up movement has been performed the predetermined number of times (step S14, Yes), the parameter detection unit 123 detects at least one lower limb parameter group from among a plurality of first lower limb maximum values V1, a plurality of lower limb minimum values V2, a plurality of second lower limb maximum values V3, a plurality of first lower limb elapsed times T1, a plurality of second lower limb elapsed times T2, and a plurality of third lower limb elapsed times T3 (step S15).

Next, the parameter detection unit 123 calculates at least one lower limb parameter from among an average of the plurality of first lower limb maximum values, an average of the plurality of lower limb minimum values, an average of the plurality of second lower limb maximum values, an average of the plurality of first lower limb elapsed times, an average of the plurality of second lower limb elapsed times, an average of the plurality of third lower limb elapsed times, a standard deviation of the plurality of first lower limb maximum values, a standard deviation of the plurality of lower limb minimum values, a standard deviation of the plurality of second lower limb maximum values, a standard deviation of the plurality of first lower limb elapsed times, a standard deviation of the plurality of second lower limb elapsed times, and a standard deviation of the plurality of third lower limb elapsed times (step S16).

Next, the lower limb muscle strength evaluation unit 124 calculates the evaluation value of the lower limb muscle strength of the user 3 using at least one of the lower limb parameters detected by the parameter detection unit 123 (step S17).

Note that the process from steps S17 to S19 illustrated in FIG. 7 is the same as the process from steps S5 to S7 illustrated in FIG. 5, and therefore a description is omitted.

As described above, by having the user 3 stand up a plurality of times, outliers can be eliminated from the acquired sensor data, and the accuracy of the acquired sensor data can be improved.

Also, in the present embodiment, the sensor device 2 is worn on only one of the left lower limb and the right lower limb of the user 3, but the present disclosure is not strictly limited thereto, and the sensor device 2 may also be worn on both the left and right lower limbs of the user 3.

In this case, the sensor data acquisition unit 122 may acquire the angle of both the left and right lower limbs of the user 3 while the user 3 stands up from a sitting state. The parameter detection unit 123 may also detect at least one lower limb parameter from among the first lower limb maximum values V1 corresponding to the left lower limb and the right lower limb, the lower limb minimum values V2 corresponding to the left lower limb and the right lower limb, the second lower limb maximum value V3 corresponding to the left lower limb and the right lower limb, the first lower limb elapsed times T1 corresponding to the left lower limb and the right lower limb, the second lower limb elapsed times T2 corresponding to the left lower limb and the right lower limb, and the third lower limb elapsed times T3 corresponding to the left lower limb and the right lower limb.

Furthermore, the parameter detection unit 123 may calculate at least one lower limb parameter from among an average of the first lower limb maximum value corresponding to the left lower limb and the first lower limb maximum value corresponding to the right lower limb, an average of the lower limb minimum value corresponding to the left lower limb and the lower limb minimum value corresponding to the right lower limb, an average of the second lower limb maximum value corresponding to the left lower limb and the second lower limb maximum value corresponding to the right lower limb, an average of the first lower limb elapsed time corresponding to the left lower limb and the first lower limb elapsed time corresponding to the right lower limb, an average of the second lower limb elapsed time corresponding to the left lower limb and the second lower limb elapsed time corresponding to the right lower limb, and an average of the third lower limb elapsed time corresponding to the left lower limb and the third lower limb elapsed time corresponding to the right lower limb.

As described above, in the period from when the user 3 is in a sitting state until the user 3 stands up, the lower limb muscle strength is evaluated on the basis of the motion of both the left lower limb and the right lower limb of the user 3, and therefore the lower limb muscle strength of the user 3 can be evaluated with higher accuracy.

Next, a specific example using the lower limb muscle strength evaluation model (multiple regression equation) will be described.

The lower limb muscle strength evaluation model is a multiple regression equation that treats the evaluation value of the lower limb muscle strength as a response variable and at least one lower limb parameter in the standing-up movement as an explanatory variable. The lower limb muscle strength evaluation unit 124 calculates the evaluation value of the lower limb muscle strength of the test subject by substituting the at least one lower limb parameter detected by the parameter detection unit 123 into the lower limb muscle strength evaluation model.

In general, the method of selecting the explanatory variable in a multiple regression equation is the stepwise method, the backward elimination method, or the forward selection method. To test all possible combinations of the plurality of lower limb parameters detected on the basis of the standing-up movement, the inventors used the forward selection method to calculate correlation coefficients between evaluation values of the lower limb muscle strength calculated by the multiple regression equation and actual evaluation values of the lower limb muscle strength.

First, a first case will be described in which the user 3 wearing the sensor device 2 on only one of the left and right lower limbs performs a single standing-up movement.

In the first case, in the case where 12 test subjects (7 male, 5 female) wearing the sensor device 2 on the left ankle each perform a single standing-up movement, the multiple regression equation for estimating the evaluation value of the lower limb muscle strength is expressed by the following Formula (2).

$$\text{Evaluation value of lower limb muscle strength} = 0.73113*(\text{first lower limb maximum value}) - 0.43449*(\text{lower limb minimum value}) + 0.1399*(\text{second lower limb maximum value}) + 1.5997*(\text{first lower limb elapsed time}) - 0.69112*(\text{third lower limb elapsed time}) + 1.063 \quad (2)$$

In the multiple regression equation expressed in Formula (2), five features (lower limb parameters) are selected, and the evaluation value of the lower limb muscle strength is estimated by the multiple regression equation. In this case, the parameter detection unit 123 detects the first lower limb maximum value, the lower limb minimum value, the second lower limb maximum value, the first lower limb elapsed time, and the third lower limb elapsed time. The lower limb muscle strength evaluation unit 124 calculates the evaluation value of the lower limb muscle strength by substituting the detected first lower limb maximum value, lower limb minimum value, second lower limb maximum value, first lower limb elapsed time, and third lower limb elapsed time into the multiple regression equation expressed in Formula (2).

Here, the inventors performed cross-validation using the above five features. Leave-one-out cross-validation was adopted as the method of cross-validation. In leave-one-out cross-validation, the data of one test subject from among the data of the 12 test subjects is left out as a test case, and the remaining test subject data is validated as training cases. Additionally, the validation is repeated 12 times so that all cases become a test case.

Figure 8:
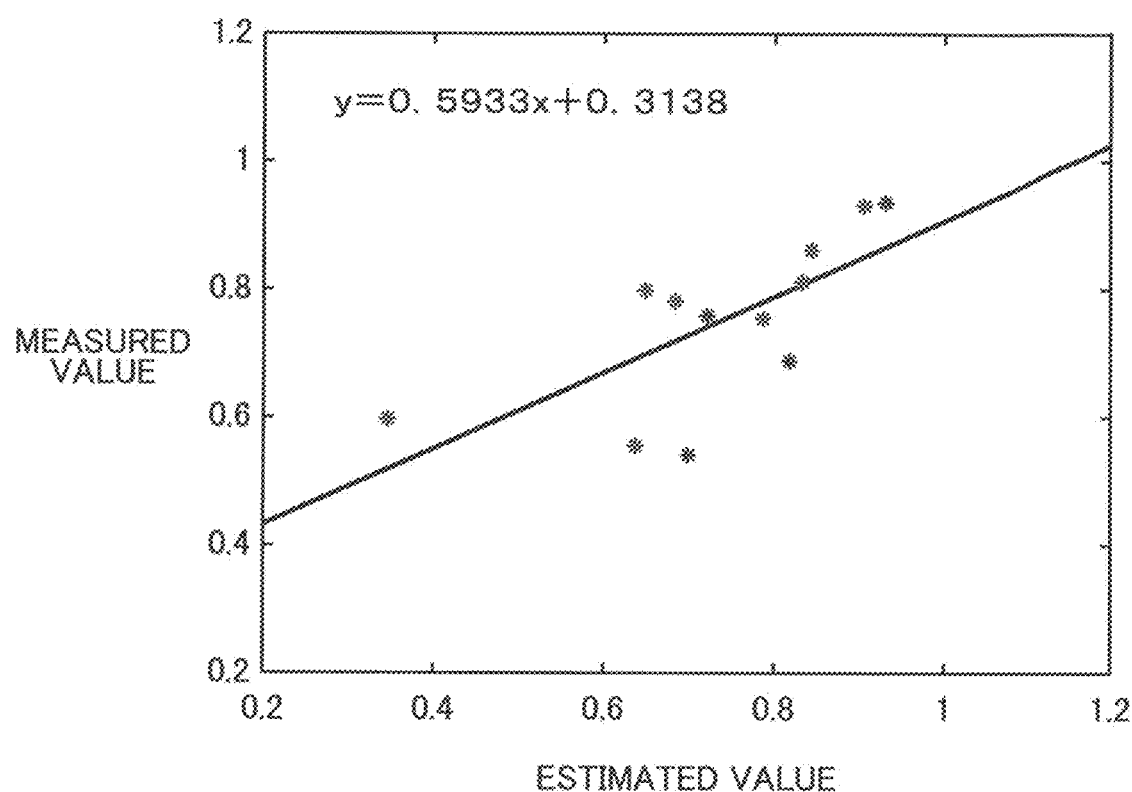
FIG. 8 is a diagram illustrating the relationship between estimated values and measured values of lower limb muscle strength evaluation values in a first case of the present embodiment.

FIG. 8 is a diagram illustrating the relationship between estimated values and measured values of lower limb muscle strength evaluation values in a first case of the present embodiment. In FIG. 8, the vertical axis represents the measured values of the evaluation value of the lower limb muscle strength, while the horizontal axis represents estimated values of the evaluation value of the lower limb muscle strength.

In the first case, the correlation coefficient between the estimated values and the measured values of the evaluation value of the lower limb muscle strength is 0.6981. Also, the relationship between an estimated value x and a measured value y of the evaluation value of the lower limb muscle strength is expressed by the following Formula (3).

$$y=0.5933x+0.3138 \qquad (3)$$

Next, a second case will be described in which the user 3 wearing the sensor device 2 on only one of the left and right lower limbs performs five times of standing-up movement.

In the second case, in the case where 12 test subjects (7 male, 5 female) wearing the sensor device 2 on the left ankle each perform five times of standing-up movement, the multiple regression equation for estimating the evaluation value of the lower limb muscle strength is expressed by the following Formula (4).

Lower limb muscle strength=0.29444*(average of first lower limb maximum value)−0.12293*(average of lower limb minimum value)+1.0616*(average of first lower limb elapsed time)+5.4164*(standard deviation of first lower limb elapsed time)−1.1437*(standard deviation of lower limb minimum value)−0.56422*(standard deviation of first lower limb maximum value)+0.14301*(standard deviation of second lower limb maximum value)+0.40275     (4)

In the multiple regression equation expressed in Formula (4), seven features (lower limb parameters) are selected, and the evaluation value of the lower limb muscle strength is estimated by the multiple regression equation. In this case, the parameter detection unit 123 detects the first lower limb maximum value, the lower limb minimum value, the second lower limb maximum value, and the first lower limb elapsed time. Additionally, the parameter detection unit 123 calculates the average of the first lower limb maximum value, the average of the lower limb minimum value, the average of the first lower limb elapsed time, the standard deviation of the first lower limb elapsed time, the standard deviation of the lower limb minimum value, the standard deviation of the first lower limb maximum value, and the standard deviation of the second lower limb maximum value. The lower limb muscle strength evaluation unit 124 calculates the evaluation value of the lower limb muscle strength by substituting the calculated average of the first lower limb maximum value, average of the lower limb minimum value, average of the first lower limb elapsed time, standard deviation of the first lower limb elapsed time, standard deviation of the lower limb minimum value, standard deviation of the first lower limb maximum value, and standard deviation of the second lower limb maximum value into the multiple regression equation expressed in Formula (4).

Here, the inventors performed cross-validation using the above seven features. Leave-one-out cross-validation was adopted as the method of cross-validation.

Figure 9:
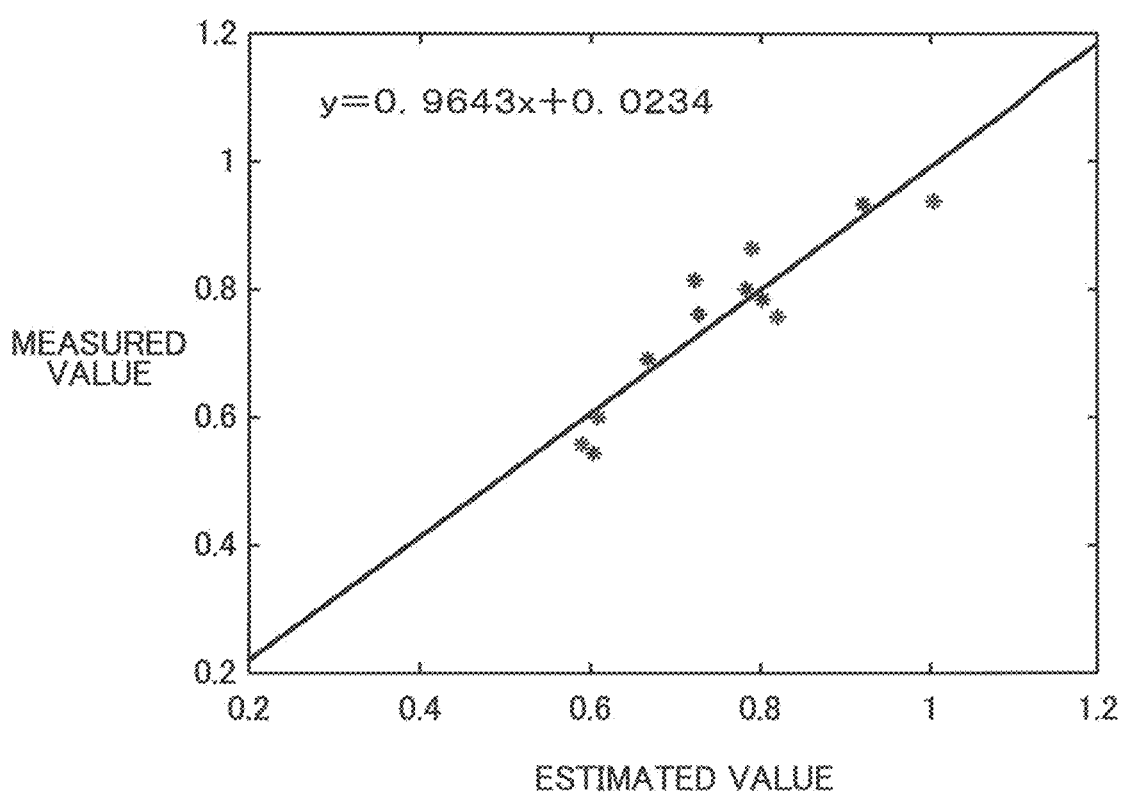
FIG. 9 is a diagram illustrating the relationship between estimated values and measured values of lower limb muscle strength evaluation values in a second case of the present embodiment.

FIG. 9 is a diagram illustrating the relationship between estimated values and measured values of lower limb muscle strength evaluation values in a second case of the present embodiment. In FIG. 9, the vertical axis represents the measured values of the evaluation value of the lower limb muscle strength, while the horizontal axis represents estimated values of the evaluation value of the lower limb muscle strength.

In the second case, the correlation coefficient between the estimated values and the measured values of the evaluation value of the lower limb muscle strength is 0.9226. Also, the relationship between an estimated value x and a measured value y of the evaluation value of the lower limb muscle strength is expressed by the following Formula (5).

$$y=0.9643x+0.0234 \qquad (5)$$

Next, a third case will be described in which the user 3 wearing the sensor device 2 on both of the left and right lower limbs performs five times of standing-up movement.

In the third case, in the case where 12 test subjects (7 male, 5 female) wearing the sensor device 2 on the both ankles each perform five times of standing-up movement, the multiple regression equation for estimating the evaluation value of the lower limb muscle strength is expressed by the following Formula (6).

Lower limb muscle strength=−0.022756*(standard deviation of first lower limb maximum value of left leg)+3.3115*(standard deviation of first lower limb elapsed time of left leg)−1.1156*(standard deviation of first lower limb maximum value averaged for both legs)+0.31363*(standard deviation of lower limb minimum value averaged for both legs)+0.12802*(standard deviation of second lower limb maximum value averaged for both legs)+0.53057     (6)

In the multiple regression equation expressed in Formula (6), five features (lower limb parameters) are selected, and the evaluation value of the lower limb muscle strength is estimated by the multiple regression equation. In this case, the parameter detection unit 123 detects the first lower limb maximum value of the left leg, the first lower limb maximum value of the right leg, the lower limb minimum value of the left leg, the lower limb minimum value of the right leg, the second lower limb maximum value of the left leg, the second lower limb maximum value of the right leg, and the first lower limb elapsed time of the left leg. Additionally, the parameter detection unit 123 calculates the standard deviation of the first lower limb maximum value of the left leg, the standard deviation of the first lower limb elapsed time of the left leg, the standard deviation of the first lower limb maximum value averaged for both legs, the standard deviation of the lower limb minimum value averaged for both legs, and the standard deviation of the second lower limb maximum value averaged for both legs. The lower limb muscle strength evaluation unit 124 calculates the evaluation value of the lower limb muscle strength by substituting the calculated standard deviation of the first lower limb maximum value of the left leg, standard deviation of the first lower limb elapsed time of the left leg, standard deviation of the first lower limb maximum value averaged for both legs, standard deviation of the lower limb minimum value averaged for both legs, and standard deviation of the second lower limb maximum value averaged for both legs into the multiple regression equation expressed in Formula (6).

Here, the inventors performed cross-validation using the above five features. Leave-one-out cross-validation was adopted as the method of cross-validation.

FIG. 10 is a diagram illustrating the relationship between estimated values and measured values of lower limb muscle strength evaluation values in the third case of the present embodiment. In FIG. 10, the vertical axis represents the measured values of the evaluation value of the lower limb muscle strength, while the horizontal axis represents estimated values of the evaluation value of the lower limb muscle strength.

In the third case, the correlation coefficient between the estimated values and the measured values of the evaluation value of the lower limb muscle strength is 0.9349. Also, the relationship between an estimated value x and a measured value y of the evaluation value of the lower limb muscle strength is expressed by the following Formula (7).

$$y=0.8723x+0.0858 \quad (7)$$

Note that in the present embodiment, the sensor data acquisition unit 122 acquires the angle of the lower limb on the basis of sensor data obtained from the sensor device 2 that includes an acceleration sensor or an angular velocity sensor, but the present disclosure is not strictly limited thereto, and may also acquire the angle of the lower limb using a motion capture system. The motion capture system may be any of an optical type, a magnetic type, a mechanical type, or an inertial sensor type. For example, an optical motion capture system uses a camera to take an image of the user 3 having markers attached to the joint portions of the lower limb, and detects the positions of the markers from the taken image. The sensor data acquisition unit 122 acquires the angle of the lower limb of the user 3 from the position data detected by the motion capture system. For example, the three-dimensional motion analysis apparatus produced by Inter Reha Co., Ltd. is usable as an optical motion capture system.

A feature of the standing-up movement treated as the explanatory variable of the multiple regression equation may be acquired from not only an acceleration sensor or an angular velocity sensor, but also from a motion capture system that acquires skeletal information from an image. Also, a plurality of features respectively obtained from a plurality of different measurement positions may be used as explanatory variables of the multiple regression equation. From the perspective of the accuracy of the regression analysis, it is preferable to treat a plurality of features as explanatory variables.

Additionally, the motion capture system may also be provided with a depth sensor and a color camera, and may automatically extract position information about the joints of the test subject from an image, and detect the posture of the test subject. In this case, markers do not have to be attached to the test subject. For example, Kinect produced by Microsoft Corporation is usable as such a motion capture system.

In the measurement of the standing-up movement using a motion capture system, it is preferable to extract the angle of the lower limb in a single standing-up movement from position coordinates, and detect a feature of the standing-up movement from the extracted angle.

Also, in the case where the motion capture system is Kinect, the motion capture system is installed at a position where the plantar flexion angle and dorsiflexion angle of the ankle during the standing-up movement are measurable, or a position where the extension angle and the flexion angle of the knee during the standing-up movement are measurable.

The motion capture system may also treat changes in plantar flexion and dorsiflexion angles of the ankle as features of the standing-up movement. The motion capture system may also treat changes in the extension and flexion angles of the knee as features of the standing-up movement.

The sensor data acquisition unit 122 may acquire the angle of lumbar of the user 3 while the user 3 stands up from a sitting state. In this case, the sensor data acquisition unit 122 may also acquire the angle of the lumbar of the user 3 in addition to the angle of the lower limb of the user 3. Note that the angle of the lumbar may be calculated from the angular velocity measured by a sensor device worn on the lumbar of the user 3, or from an image taken by a motion capture system.

Further, the parameter detection unit 123 may detect at least one lumbar parameter of a first lumbar maximum value indicating the angle when a lumbar is initially inclined the most in a first direction, a lumbar minimum value indicating the angle when the lumbar is inclined the most in a second direction that is opposite the first direction, a second lumbar maximum value indicating the angle when the lumbar is again inclined the most in the first direction, a first lumbar elapsed time from the point in time when the user 3 begins to stand up until the point in time when the first lumbar maximum value is detected, a second lumbar elapsed time from the point in time when the user 3 begins to stand up until the point in time when the lumbar minimum value is detected, or a third lumbar elapsed time from the point in time when the user 3 begins to stand up until the point in time when the second lumbar maximum value is detected.

Additionally, the lower limb muscle strength evaluation unit 124 may also evaluate the lower limb muscle strength of the user 3 using at least one lower limb parameter and at least one lumbar parameter. In this case, the lower limb muscle strength evaluation unit 124 may calculate an evaluation value of the lower limb muscle strength by substituting at least one detected lower limb parameter and at least one detected lumbar parameter into a multiple regression equation that treats the evaluation value of the lower limb muscle strength as a response variable and the at least one lower limb parameter and at least one lumbar parameter as an explanatory variable.

As describe above, in the period from when the user 3 is in a sitting state until the user 3 stands up, the lower limb muscle strength is evaluated on the basis of the motion of the lumbar of the user 3 and the motion of the lower limbs of the user 3, and therefore the lower limb muscle strength of the user 3 can be evaluated with higher accuracy.

Note that, in the above respective embodiments, each structural element may be configured by dedicated hardware, or realized by executing a software program suited to each structural element. Each structural element may be realized as a result of a program execution unit such as a CPU or processor reading out and executing a software program recorded on a recording medium such as a hard disk or semiconductor memory.

Some or all of the functions of a device according to an embodiment of the present disclosure are typically achieved as an integrated circuit, namely a large-scale integration (LSI) chip. The functions may be realized individually as discrete chips, or as a single chip containing some or all of the functions. Furthermore, the circuit integration methodology is not limited to LSI, and may also be realized with special-purpose circuits or general-purpose processors. A field-programmable gate array (FPGA) capable of being programmed after LSI fabrication, or a reconfigurable processor whose internal LSI circuit cell connections and settings may be reconfigured, may also be used.

In addition, some or all of the functions of a device according to an embodiment of the present disclosure may be achieved by having a processor such as a CPU execute a program.

The numbers used above are all illustrative examples for specifically describing the present disclosure, and the present disclosure is not limited to the numbers given as examples.

Also, the order of execution of the steps illustrated in the above flowcharts is an illustrative example for specifically describing the present disclosure, and an order other than the above is acceptable insofar as a similar effect is obtained. Also, some of the above steps may also be executed at the same time as (in parallel with) other steps.

The technology according to the present disclosure makes it possible to easily evaluate the lower limb muscle strength of a user with high accuracy, and therefore is useful as a technology for evaluating the lower limb muscle strength of a user.

This application is based on U.S. Provisional application No. 62/854,053 filed in United States Patent and Trademark Office on May 29, 2019 and Japanese Patent application No. 2019-168397 filed in Japan Patent Office on Sep. 17, 2019, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. A lower limb muscle strength evaluation method executed by a computer, the method comprising:
acquiring an angle of at least one of left and right lower limbs of a user while the user stands up from a sitting state by using a sensor device which is worn between a knee and an ankle of the user;
detecting at least one lower limb parameter from among a first lower limb maximum value indicating the angle when the lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from a point in time when the user begins to stand up until a point in time when the first lower limb maximum value is detected, a second lower limb elapsed time from the point in time when the user begins to stand up until a point in time when the lower limb minimum value is detected, and a third lower limb elapsed time from the point in time when the user begins to stand up until a point in time when the second lower limb maximum value is detected;
evaluating a lower limb muscle strength of the user using the at least one lower limb parameter; and
outputting an evaluation result,
wherein the angle of the lower limb is an angle defined by a straight line extending from a knee in a vertical direction and a straight line connecting the knee and an ankle,
when the lower limb of the user is parallel to the vertical direction, the angle of the lower limb is 0 degrees,
at least one lower limb parameter group from among a plurality of first lower limb maximum values, a plurality of lower limb minimum values, a plurality of second lower limb maximum values, a plurality of first lower limb elapsed times, a plurality of second lower limb elapsed times, and a plurality of third lower limb elapsed times is detected by having the user stand up a plurality of times,
the method further comprising calculating at least one lower limb parameter from among an average of the plurality of first lower limb maximum values, an average of the plurality of lower limb minimum values, an average of the plurality of second lower limb maximum values, an average of the plurality of first lower limb elapsed times, an average of the plurality of second lower limb elapsed times, an average of the plurality of third lower limb elapsed times, a standard deviation of the plurality of first lower limb maximum values, a standard deviation of the plurality of lower limb minimum values, a standard deviation of the plurality of second lower limb maximum values, a standard deviation of the plurality of first lower limb elapsed times, a standard deviation of the plurality of second lower limb elapsed times, and a standard deviation of the plurality of third lower limb elapsed times.

2. The lower limb muscle strength evaluation method according to claim 1, further comprising:
acquiring the angle on a basis of sensor data obtained from a sensor worn on at least one of the left and right lower limbs of the user.

3. The lower limb muscle strength evaluation method according to claim 1, wherein the angle is acquired using a motion capture system.

4. The lower limb muscle strength evaluation method according to claim 1, wherein
the angles of both the left lower limb and the right lower limb of the user are acquired while the user stands up from a sitting state, and
at least one lower limb parameter from among the first lower limb maximum values corresponding to the left lower limb and the right lower limb, the lower limb minimum values corresponding to the left lower limb and the right lower limb, the second lower limb maximum value corresponding to the left lower limb and the right lower limb, the first lower limb elapsed times corresponding to the left lower limb and the right lower limb, the second lower limb elapsed times corresponding to the left lower limb and the right lower limb, and the third lower limb elapsed times corresponding to the left lower limb and the right lower limb are detected,
the method further comprising calculating at least one lower limb parameter from among an average of the first lower limb maximum value corresponding to the left lower limb and the first lower limb maximum value corresponding to the right lower limb, an average of the lower limb minimum value corresponding to the left lower limb and the lower limb minimum value corresponding to the right lower limb, an average of the second lower limb maximum value corresponding to the left lower limb and the second lower limb maximum value corresponding to the right lower limb, an average of the first lower limb elapsed time corresponding to the left lower limb and the first lower limb elapsed time corresponding to the right lower limb, an average of the second lower limb elapsed time corresponding to the left lower limb and the second lower limb elapsed time corresponding to the right lower limb, and an average of the third lower limb elapsed time corresponding to the left lower limb and the third lower limb elapsed time corresponding to the right lower limb.

5. The lower limb muscle strength evaluation method according to claim 1, wherein the evaluation value of the lower limb muscle strength is calculated by substituting the at least one detected lower limb parameter into a multiple regression equation that treats the evaluation value of the lower limb muscle strength as a response variable and the at least one lower limb parameter as an explanatory variable.

6. The lower limb muscle strength evaluation method according to claim 1, further comprising:
acquiring an angle of a lumbar of the user while the user stands up from a sitting state; and
detecting at least one lumbar parameter from among a first lumbar maximum value indicating the angle when the lumbar is initially inclined the most in a first direction, a lumbar minimum value indicating the angle when the lumbar is inclined the most in a second direction that is opposite the first direction, a second lumbar maximum value indicating the angle when the lumbar is again inclined the most in the first direction, a first lumbar elapsed time from a point in time when the user begins to stand up until a point in time when the first lumbar maximum value is detected, a second lumbar elapsed time from the point in time when the user begins to stand up until a point in time when the lumbar minimum value is detected, and a third lumbar elapsed time from the point in time when the user begins to stand up until a point in time when the second lumbar maximum value is detected, wherein
the lower limb muscle strength of the user is evaluated using the at least one lower limb parameter and the at least one lumbar parameter.

7. The lower limb muscle strength evaluation method according to claim 1, wherein the sensor is on a front portion of the ankle.

8. A non-transitory computer-readable recording medium storing a lower limb muscle strength evaluation program causing a computer to execute a process comprising:
acquiring an angle of at least one of left and right lower limbs of a user while the user stands up from a sitting state by using a sensor device which is worn between a knee and an ankle of the user;
detecting at least one lower limb parameter from among a first lower limb maximum value indicating the angle when the lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from a point in time when the user begins to stand up until a point in time when the first lower limb maximum value is detected, a second lower limb elapsed time from the point in time when the user begins to stand up until a point in time when the lower limb minimum value is detected, and a third lower limb elapsed time from the point in time when the user begins to stand up until a point in time when the second lower limb maximum value is detected;
evaluating a lower limb muscle strength of the user using the at least one lower limb parameter; and
outputting an evaluation result, wherein
the angle of the lower limb is an angle defined by a straight line extending from a knee in a vertical direction and a straight line connecting the knee and an ankle,
when the lower limb of the user is parallel to the vertical direction, the angle of the lower limb is 0 degrees,
at least one lower limb parameter group from among a plurality of first lower limb maximum values, a plurality of lower limb minimum values, a plurality of second lower limb maximum values, a plurality of first lower limb elapsed times, a plurality of second lower limb elapsed times, and a plurality of third lower limb elapsed times is detected by having the user stand up a plurality of times,
the lower limb muscle strength evaluation program causing the computer to execute the process further comprising:
calculating at least one lower limb parameter from among an average of the plurality of first lower limb maximum values, an average of the plurality of lower limb minimum values, an average of the plurality of second lower limb maximum values, an average of the plurality of first lower limb elapsed times, an average of the plurality of second lower limb elapsed times, an average of the plurality of third lower limb elapsed times, a standard deviation of the plurality of first lower limb maximum values, a standard deviation of the plurality of lower limb minimum values, a standard deviation of the plurality of second lower limb maximum values, a standard deviation of the plurality of first lower limb elapsed times, a standard deviation of the plurality of second lower limb elapsed times, and a standard deviation of the plurality of third lower limb elapsed times.

9. The non-transitory computer-readable recording medium according to claim 8, wherein the lower limb muscle strength evaluation program causes the computer to execute the process in which the sensor is on a front portion of the ankle.

10. A lower limb muscle strength evaluation device comprising:
a memory configured to store a program; and
a processor configured to execute the program and control the lower limb muscle strength evaluation device to:
acquire an angle of at least one of left and right lower limbs of a user while the user stands up from a sitting state by using a sensor device which is worn between a knee and an ankle of the user;
detect at least one lower limb parameter from among a first lower limb maximum value indicating the angle when the lower limb is initially inclined the most in a first direction, a lower limb minimum value indicating the angle when the lower limb is inclined the most in a second direction that is opposite the first direction, a second lower limb maximum value indicating the angle when the lower limb is again inclined the most in the first direction, a first lower limb elapsed time from a point in time when the user begins to stand up until a point in time when the first lower limb maximum value is detected, a second lower limb elapsed time from the point in time when the user begins to stand up until a point in time when the lower limb minimum value is detected, and a third lower limb elapsed time from the point in time when the user begins to stand up until a point in time when the second lower limb maximum value is detected;

evaluate a lower limb muscle strength of the user using the at least one lower limb parameter; and output an evaluation result, wherein the angle of the lower limb is an angle defined by a straight line extending from a knee in a vertical direction and a straight line connecting the knee and an ankle, when the lower limb of the user is parallel to the vertical direction, the angle of the lower limb is 0 degrees, the processor detects at least one lower limb parameter group from among a plurality of first lower limb maximum values, a plurality of lower limb minimum values, a plurality of second lower limb maximum values, a plurality of first lower limb elapsed times, a plurality of second lower limb elapsed times, and a plurality of third lower limb elapsed times by having the user stand up a plurality of times, the processor further calculates at least one lower limb parameter from among an average of the plurality of first lower limb maximum values, an average of the plurality of lower limb minimum values, an average of the plurality of second lower limb maximum values, an average of the plurality of first lower limb elapsed times, an average of the plurality of second lower limb elapsed times, an average of the plurality of third lower limb elapsed times, a standard deviation of the plurality of first lower limb maximum values, a standard deviation of the plurality of lower limb minimum values, a standard deviation of the plurality of second lower limb maximum values, a standard deviation of the plurality of first lower limb elapsed times, a standard deviation of the plurality of second lower limb elapsed times, and a standard deviation of the plurality of third lower limb elapsed times.

11. A lower limb muscle strength evaluation system comprising:

the lower limb muscle strength evaluation device according to claim 10; and a sensor that is worn on at least one of the left and right lower limbs of the user and that transmits measured sensor data to the lower limb muscle strength evaluation device.

12. The lower limb muscle strength evaluation device according to claim 10, wherein the sensor is on a front portion of the ankle.

* * * * *